US009333039B2

(12) United States Patent
Kuchenbecker et al.

(10) Patent No.: US 9,333,039 B2
(45) Date of Patent: May 10, 2016

(54) SYSTEMS AND METHODS FOR PROVIDING VIBRATION FEEDBACK IN ROBOTIC SYSTEMS

(75) Inventors: Katherine J. Kuchenbecker, Philadelphia, PA (US); Dorsey Standish, Potomac, MD (US); William McMahan, Philadelphia, PA (US); Jamie Gewirtz, Wyndmoor, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 748 days.

(21) Appl. No.: 13/577,581

(22) PCT Filed: Feb. 8, 2011

(86) PCT No.: PCT/US2011/023995
§ 371 (c)(1),
(2), (4) Date: Aug. 7, 2012

(87) PCT Pub. No.: WO2011/100220
PCT Pub. Date: Aug. 18, 2011

(65) Prior Publication Data
US 2012/0310257 A1    Dec. 6, 2012

Related U.S. Application Data

(60) Provisional application No. 61/302,681, filed on Feb. 9, 2010.

(51) Int. Cl.
*A61B 19/00* (2006.01)
*G06F 19/00* (2011.01)
(Continued)

(52) U.S. Cl.
CPC ..... *A61B 19/2203* (2013.01); *A61B 2019/2292* (2013.01)

(58) Field of Classification Search
CPC ............... A61B 2019/464; A61B 2017/00022; A61B 2019/2292; A61B 17/00234; G05B 2219/40144
See application file for complete search history.

(56) References Cited

U.S. PATENT DOCUMENTS 4,655,673 A * 4/1987 Hawkes ......................... 414/730
6,184,868 B1 * 2/2001 Shahoian et al. ............. 345/161
(Continued)

OTHER PUBLICATIONS

D. Kontarinis, et al., "Tactile Display of Vibratory Information in Teleoperation and Virtual Environments", 4(4):387-402, 1995.
(Continued)

*Primary Examiner* — Khoi Tran
*Assistant Examiner* — Dale Moyer
(74) *Attorney, Agent, or Firm* — RatnerPrestia

(57) ABSTRACT

Systems and methods for providing vibration feedback in robotic systems are disclosed. A system for configuring a robotic surgery system to provide vibration feedback during robot-assisted surgery includes a sensor, an actuator, and a controller. The sensor is coupled to the robotic surgery system such that the sensor senses a vibration of a surgical tool. The actuator is coupled to the surgery system such that the actuator provides a vibration to a user at a control station. The controller is electrically coupled with the sensor and the actuator. The controller is configured to receive data corresponding to a sensed vibration from the sensor. The controller is further configured to actuate the actuator based on the received data such that the actuator provides a vibration to the user when the sensor senses the vibration of the tool. The above system may be configured to provide tactile and/or audio feedback.

28 Claims, 14 Drawing Sheets

(51) Int. Cl.
 *A61B 17/94* (2006.01)
 *G06F 3/01* (2006.01)

(56) References Cited

U.S. PATENT DOCUMENTS

| | | | |
|---|---|---|---|
| 6,232,891 B1 | 5/2001 | Rosenberg | |
| 6,697,044 B2* | 2/2004 | Shahoian et al. | 345/156 |
| 6,810,281 B2* | 10/2004 | Brock et al. | 600/427 |
| 7,864,173 B2 | 1/2011 | Handley et al. | |
| 7,963,770 B2 | 6/2011 | Kukora | |
| 7,997,126 B2 | 8/2011 | Kang et al. | |
| 8,016,818 B2 | 9/2011 | Ellis et al. | |
| 8,190,292 B2 | 5/2012 | Niemeyer et al. | |
| 2004/0233167 A1 | 11/2004 | Braun et al. | |
| 2006/0005613 A1 | 1/2006 | Kuwajima et al. | |
| 2006/0279537 A1 | 12/2006 | Kim et al. | |
| 2007/0001638 A1 | 1/2007 | Gray et al. | |
| 2007/0135735 A1* | 6/2007 | Ellis et al. | 600/587 |
| 2008/0012826 A1 | 1/2008 | Cunningham et al. | |
| 2009/0012532 A1 | 1/2009 | Quaid et al. | |
| 2009/0163929 A1* | 6/2009 | Yeung et al. | 606/130 |
| 2010/0013653 A1 | 1/2010 | Birnbaum et al. | |
| 2010/0261526 A1 | 10/2010 | Anderson et al. | |
| 2011/0046659 A1* | 2/2011 | Ramstein et al. | 606/205 |
| 2011/0285637 A1 | 11/2011 | Karkkainen | |
| 2012/0026180 A1* | 2/2012 | Kuchenbecker | G06F 3/016 345/582 |
| 2012/0310257 A1 | 12/2012 | Kuchenbecker et al. | |

OTHER PUBLICATIONS

McMahan et al., "Haptic Display of Realistic Tool Contact Via Dynamically Compensated Control of a Dedicated Actuator", 2009 IEEE/RSJ International Conference, pp. 3170-3177.
D. Kontarinis, et al., "A Multiparameter Tactile Display System for Teleoperation", pp. 103-108, 1995.
International Search Report and Written Opinion dated Apr. 6, 2011, application No. PCT/US11/23995.
Kuchenbecker, Katherine J., "Haptography: Capturing the Feel of Real Objects to Enable Authentic Haptic Rendering (Invited Paper)", HAS '08 (Feb. 11-14, 2008), 3 pgs.
Landin, Nils, "Dimensional Reduction of High-Frequency Accelerations for Haptic Rendering", EuroHaptics, Part II, LNCS 6192 (2010), 79-86.
Okamura, A. M., "Measurement-Based Modeling for Haptic Rendering", Haptic Rendering (Jul. 2008), 445-469 Iii.
Romano, Joseph M., "Automatic Filter Design for Synthesis of Haptic Textures from Recorded Acceleration Data", IEEE International Conference on Robotics and Automation, (May 3-7, 2010), 1815-1821.
International Search Report dated Jun. 20, 2014, application No. PCT/US2014/021145.
"A Tactile Magnification Instrument for Minimally Invasive Surgery", Hsin-Yun Yao et al., 2004, LNCS 3217, pp. 89-96.
"Vibrotactile Feedback for Industrial Telemanipulators", Jack Dennerlein et al, ASME IMECE, Dallas, Nov. 15-21, 1997, pp. 1-7.
"Touch Magnifying Instrument Applied to Minimally Invasive Surgery", Hsin-Yun Yao, Department of Electrical & Computer Engineering, Sep. 2004, pp. 1-55.

* cited by examiner

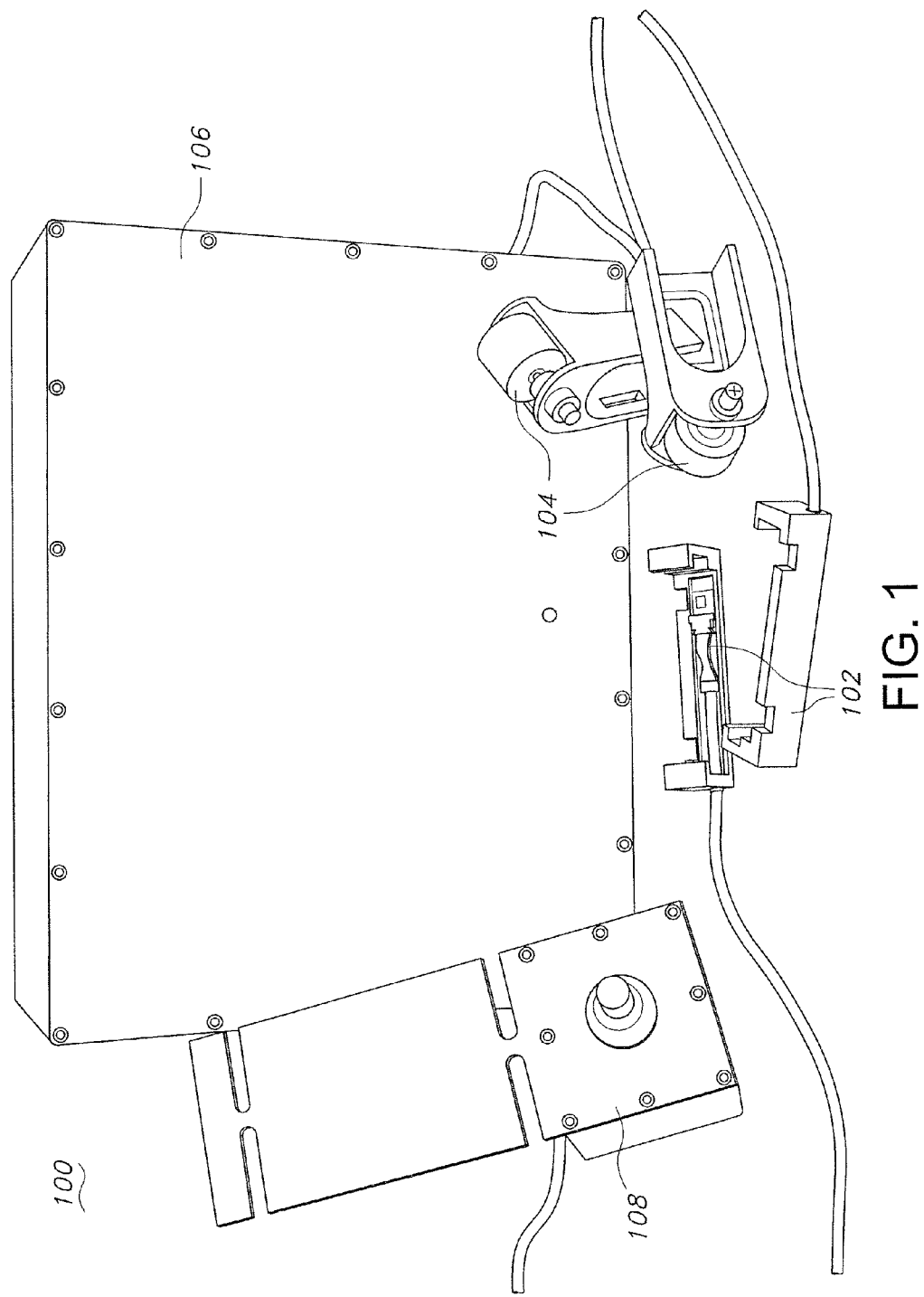

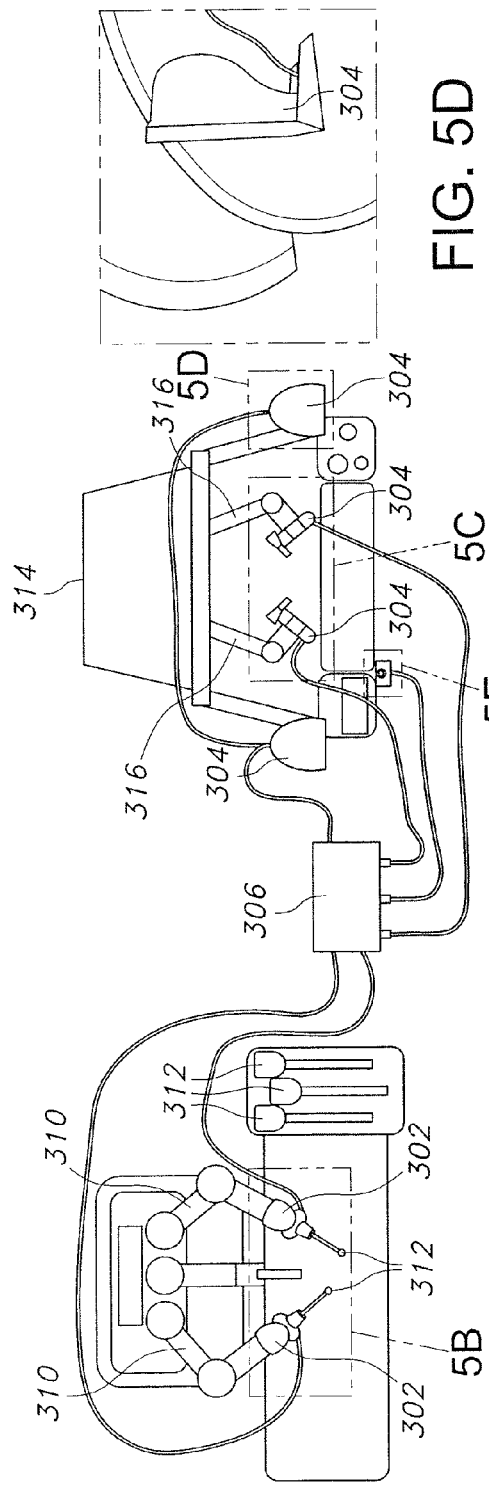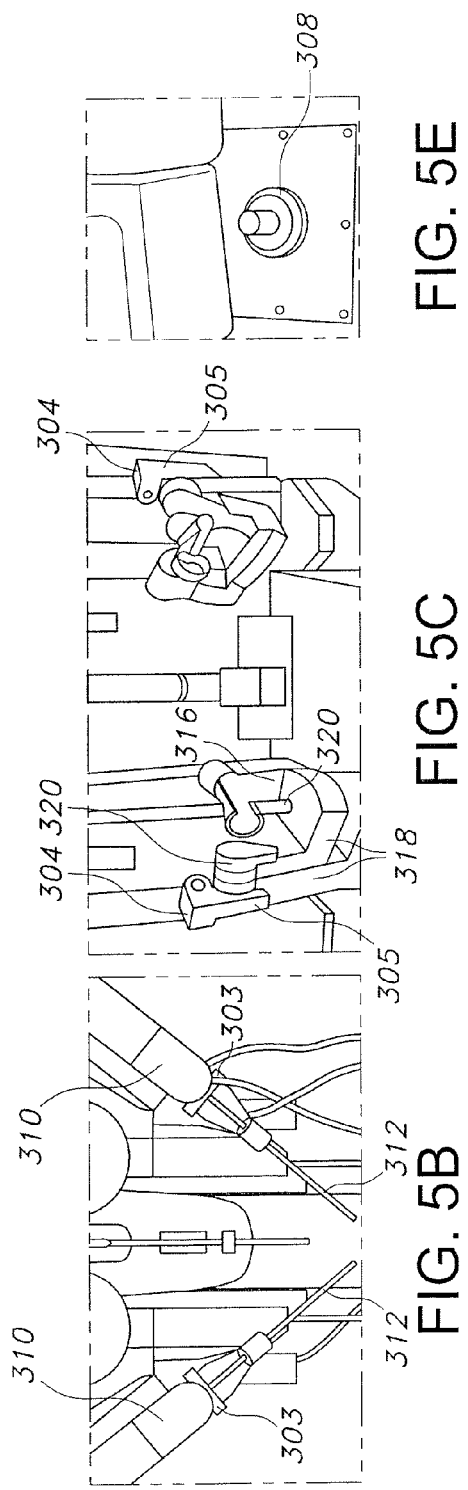

SYSTEMS AND METHODS FOR PROVIDING VIBRATION FEEDBACK IN ROBOTIC SYSTEMS

CROSS-REFERENCE TO RELATED APPLICATIONS

This application is the U.S. National Phase application of PCT International Application No. PCT/US2011/023995, filed Feb. 8, 2011, and claims priority to provisional application Ser. No. 61/302,681, filed Feb. 9, 2010, which applications are incorporated herein by reference in their entireties and for all purposes.

FIELD OF THE INVENTION

The present invention relates generally to robotic systems, and more particularly to providing vibration feedback for users of robotic systems.

BACKGROUND OF THE INVENTION

Generally, robotic systems are useful for performing tasks that humans are otherwise unable or unwilling to perform. Robotic systems may be particularly useful for performing tasks that require a strength, dexterity, size, or visualization that humans cannot easily replicate. One example of such a robotic system is a robotic surgery system, i.e., a robotic system that assists surgeons in performing surgical procedures.

For certain tasks, it may be desirable that the robotic system include a robotic component that is remotely controlled by a human operator. A human operator may control the robotic component in its performance of the desired task. However, certain tasks, e.g. surgeries, may require very precise movements by the robotic component, and therefore, very precise control by the operator of the robotic system. To achieve the required control, the human operator may rely on visual feedback, i.e., watching the robotic component, to perform the task. Nonetheless, improved robotic systems are desired for performing all types of tasks.

SUMMARY OF THE INVENTION

Aspects of the present invention are related to systems and methods for providing vibration feedback in robotic systems.

In accordance with one aspect of the present invention, a robotic surgery system includes an armature, a control station, a sensor, an actuator, and a controller. The armature is configured to manipulate a surgical tool. The control station is positioned remote from the armature. The control station has a control handle configured to operate the armature. The sensor is positioned to sense a vibration of the surgical tool. The actuator is positioned to provide a vibration to the control handle of the control station. The controller is in communication with the sensor and the actuator. The controller is configured to receive data from the sensor corresponding to a sensed vibration. The controller is further configured to actuate the actuator based on the received data such that the actuator provides a vibration to the control handle when the sensor senses the vibration of the surgical tool.

In accordance with another aspect of the present invention, a method for providing vibration feedback during robot-assisted surgery includes operating an armature of a robotic surgical system using a control handle of a remotely positioned control station of the robotic surgical system, sensing a vibration of a surgical tool with a sensor while the surgical tool is coupled to the armature of the robotic surgical system, and actuating an actuator to provide a vibration to a control handle of the control station of the robotic surgical system when the sensor senses the vibration of the tool.

In accordance with yet another aspect of the present invention, a system for configuring a robotic surgery system to provide vibration feedback during robot-assisted surgery includes a sensor, an actuator, and a controller. The robotic surgery system includes an armature for manipulating a surgical tool and a control station having a control handle for operating the armature. The sensor is configured for coupling to the robotic surgery system such that the sensor senses a vibration of the surgical tool. The actuator is configured for coupling to the surgery system such that the actuator provides a vibration to the control handle. The controller is configured to be electrically coupled with the sensor and the actuator. The controller is configured to receive data corresponding to a sensed vibration from the sensor. The controller is further configured to actuate the actuator based on the received data such that the actuator provides a vibration to the control handle when the sensor senses the vibration of the tool.

In accordance with still another aspect of the present invention, a method for configuring a robotic surgery system to provide vibration feedback during robot-assisted surgery includes coupling a sensor to the robotic surgical system such that the sensor senses a vibration of a surgical tool, coupling an actuator to the surgical system such that the actuator provides a vibration to a control handle, and electrically coupling a controller with the sensor and the actuator. The controller is configured to receive data corresponding to a sensed vibration from the sensor. The controller is further configured to actuate the actuator based on the received data such that the actuator provides a vibration to the control handle when the sensor senses the vibration of the tool.

In accordance with another aspect of the present invention, a robotic surgery system includes an armature, a control station, a sensor, an actuator, and a controller. The armature is configured to manipulate a surgical tool. The control station is positioned remote from the armature. The control station has a control handle configured to operate the armature. The sensor is coupled to sense a signal such as a sound or an audio signal or a vibration generated by the surgical tool. The actuator is coupled to provide an audio signal to an operator of the control handle. The controller is in communication with the sensor and the actuator. The controller is configured to receive data corresponding to a sensed signal from the sensor. The controller is further configured to actuate the actuator based on the received data such that the actuator provides an audio signal to an operator of the control handle when the sensor senses the signal generated by the tool.

In accordance with yet another aspect of the present invention, a robotic system includes a robotic component, a control station, a sensor, an actuator, and a controller. The control station is positioned remote from the robotic component. The control station has a control handle configured for operating the robotic component. The sensor is coupled to sense a vibration of the robotic component. The actuator is coupled to provide a vibration to the control handle. The controller is in communication with the sensor and the actuator. The controller is configured to receive data corresponding to a sensed vibration from the sensor. The controller is further configured to actuate the actuator based on the received data such that the actuator provides a vibration to the control handle when the sensor senses the vibration of the robotic component.

In accordance with still another aspect of the present invention, a method for performing robot-assisted surgery includes manipulating a surgical tool coupled to a robotic armature of a robotic surgery system using a control handle of a control station positioned remotely from the robotic armature, thereby generating a vibration of the surgical tool. A vibration is received at the control handle of the control station, the received vibration at the control handle corresponding to the generated vibration of the surgical tool.

In accordance with yet another aspect of the present invention, a robotic surgery system includes an armature, a control station, a sensor, an actuator, and a controller. The armature is configured for manipulating a surgical tool. The control station is positioned remote from the armature and has a control handle configured for operating the armature. The sensor is positioned to sense a vibration of the surgical tool. The actuator is positioned to provide a vibration at the control station. The controller is in communication with the sensor and the actuator. The controller is configured to receive data from the sensor corresponding to a sensed vibration. The controller is further configured to actuate the actuator based on the received data such that the actuator provides a vibration at the control station.

In accordance with another aspect of the present invention, a method for providing vibration feedback during robot-assisted surgery includes operating an armature of a robotic surgical system from a remotely positioned control station of a robotic surgical system, sensing a vibration of a surgical tool with a sensor while the surgical tool is coupled to the armature of the robotic surgical system, and actuating an actuator to provide a vibration at the control station of the robotic surgical system when the sensor senses the vibration of the tool.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features may be arbitrarily expanded or reduced for clarity. Included in the drawings are the following figures:

FIG. 1 depicts an exemplary embodiment of a system for configuring a robotic surgery system to provide vibration feedback during robot-assisted surgery in accordance with aspects of the present invention;

FIG. 5A depicts an exemplary embodiment of a robotic surgical system in accordance with aspects of the present invention;

FIG. 5B depicts an exemplary embodiment of a robotic armature of the system of FIG. 5A;

FIG. 5C depicts an exemplary embodiment of a control handle of the system of FIG. 5A;

FIG. 5D depicts an exemplary embodiment of an actuator of the system of FIG. 5A

FIG. 5E depicts an exemplary embodiment of an amplitude controller of the system of FIG. 5A;

DETAILED DESCRIPTION OF THE INVENTION

Figure 2A:
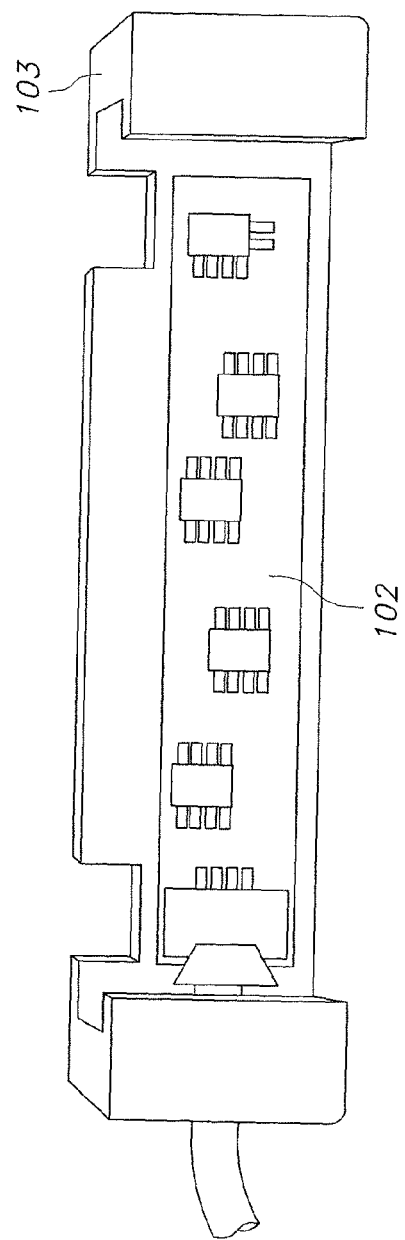
FIG. 2A depicts an exemplary embodiment of a sensor assembly of the system of FIG. 1.

The exemplary systems and methods disclosed herein are suitable for integration with robotic systems. For example, the system components described herein may be integrated with a robotic system having a remotely controlled robotic component. Suitable robotic systems may include a control station by which an operator may remotely operate the robotic component. The control station may include one or more control handles that are manipulated by the operator in operating the robotic component. In this configuration, the motions of the control handles may be transmitted to the robotic component, which will perform corresponding motions. An exemplary robotic system for use with the present invention is the DA VINCI Surgical System, provided by Intuitive Surgical, Inc.

The exemplary systems and methods disclosed herein may be particularly useful for use in conjunction with robotic surgical systems. As will be described below, the systems and methods disclosed herein may provide sensory feedback such as vibration feedback during the performance of a robot-assisted surgery, i.e., a surgery employing a robotic surgery system. As used herein, the term "vibration feedback" is intended to encompass tactile feedback as well as audio feedback. The vibration feedback may augment the surgeon's sensory experience during operations, thereby reducing cognitive load, and enabling a surgeon to perform robot-assisted surgeries more precisely, more quickly, and/or with greater ease and pleasure.

Although the systems and methods described below generally relate to robotic surgical systems, it is contemplated that aspects of the present invention may be used with non-surgical robotic systems without departing from the spirit and scope of the present invention. In other words, the present invention may be useful with medical robotic systems other than surgical robotic systems or with non-medical robotic systems.

For example, tactile feedback can benefit any robotic system in which a user's sense of touch is dissociated from a robotic tool. This includes, for example, any system in which the user is remote from a robotic tool (i.e., a system in which the hands of the user are not in direct contact with the tool). In the context of surgical robotic systems according to aspects of the invention, this encompasses any surgical system in which the hands of the surgeon are not in direct contact with the surgical tool (e.g., endoscopic or other minimally invasive surgical devices) that manipulates the patient. In other words, any system could benefit where the user-master interface (e.g., the interface between the surgeon and the controls of a surgical robotic system) does not otherwise approximate the slave-subject interface (e.g., the interface between the robot's tools and the patient's body in a surgical robotic system) in a tactile sense.

Specifically, doctors often use long thin tools to reach deep within a patient's body, which separates the doctors from the site of the intervention. In the case of a surgical robot system, these tools may be stiff rods, so the vibrations are transmitted to the robot arms holding the tools.

In other applications, the vibration sensor is optionally attached to the tool itself, perhaps located deep in the body. Endoscopic procedures, for example, use a lens on the end of a flexible instrument (an endoscope) to look into a patient's throat, and colonoscopies explore the bowels in a similar way. In both of these cases, the doctor (typically a gastroenterologist) is visually examining the tissue for signs of irregularity. Suspicious patches are biopsied by sending a thin flexible tool down the working channel of the scope. Maneuvering this biopsy tool is quite challenging, and it may benefit the doctor to be able to receive tactile signals during the manipulation.

Venous access is another potential application for aspects of this invention, in which doctors pass thin catheters from outside the body up through a vein or an artery to get to the heart or other anatomical structures. Doctors may be operating based on low-quality images, such as a 2D fluoro image, where anatomical structures are hard to see. Injecting contrast dye helps them to see better, but they have virtually no sense of touch. In such an application, a vibration sensor is optionally placed at the tip of the catheter.

Beyond medicine, there are many cases when a human operator controls a robot that is in a distant and/or hazardous environment. For example, defusing improvised explosive devices in a war zone is one example of such an application. Performing more sophisticated actions like opening doors or searching disaster scenes will require better feedback for the operator. In such instances, vibrotactile feedback would be beneficial.

Exploring the deep ocean or other hostile areas would benefit from this invention, especially if the robot needs to directly manipulate its environment. Even just driving a wheeled robot around could be made easier if one could feel the type of terrain that it is traversing.

Referring now to the drawings, FIG. 1 illustrates an exemplary system 100 for configuring a robotic surgery system to provide vibration feedback during robot-assisted surgery in accordance with an aspect of the present invention. System 100 may configure the robotic surgery system to provide tactile feedback and/or audio feedback to a user. Suitable robotic surgery systems usable with system 100 may include an armature for manipulating a surgical tool and a control station having a control handle for operating the armature. As an overview, system 100 includes a sensor 102, actuators 104, controller 106, and amplitude controller 108. Additional details of system 100 are described below.

Sensor 102 is configured to be coupled to a robotic surgery system. In an exemplary embodiment, sensor 102 is configured to be coupled to a robotic surgery system in a location where sensor 102 can sense a vibration of a surgical tool or a sound made by the surgical tool. Sensor 102 may be configured to be mounted directly to an armature of the surgical system near the base of the surgical tool. It may be desirable to mount sensor 102 to the system armature, rather than directly to the surgical tool being manipulated, in order to avoid remounting sensor 102 whenever a surgical tool is changed, and because high-frequency vibrations and sounds (like those sensed by sensor 102) transmit well through solid objects. Additionally, sensor 102 may be configured to be mounted in an area of the robotic surgery system that is outside of a sterile area. A robotic surgery system may have a sterile area corresponding to an area in which an operation will be performed on a patient. It may be desirable to mount sensor 102 outside of this sterile area in order to avoid having to sterilize sensor 102.

While two sensors 102 are illustrated, it will be understood that system 100 may include any number of sensors 102. For example, system 100 may include one sensor for each armature or surgical tool employed by the robotic surgery system. Additionally, system 100 may include multiple sensors for each armature or surgical tool employed by the robotic surgery system.

Sensor 102 is configured to sense a vibration of the surgical tool. During a surgical procedure, high-frequency vibrations may naturally occur during hard contact, cutting, rubbing, puncture, and a host of other actions with the surgical tool. The vibrations sensed by sensor 102 may desirably be these high frequency vibrations, between about 10 Hz and 1000 Hz. The vibrations sensed by sensor 102 may also include audible sounds in this frequency range. The system is optionally reconfigurable so that one can change the bandwidth to suit a particular application or a user's preference. For example, the passband could be adjusted to start below or above 10 Hz, end below or above 1000 Hz, and optionally remove intermediate frequency ranges.

In an exemplary embodiment, sensor 102 is an accelerometer. The accelerometer may include multiple measurement axes for measuring the vibration of the surgical tool in multiple dimensions. A suitable accelerometer for use as sensor 102 includes, for example, a MEMS-based high-bandwidth accelerometer, capacitive accelerometers, piezoelectric or piezoresistive accelerometers, Hall effect accelerometers, magnetoresistive accelerometers, or heat transfer accelerometers, or other suitable accelerometers. In one embodiment, for example, ADXL322 chips provided by Analog Devices, Inc. are optionally used. Alternatively, sensor 102 may be the LIS344ALH three-axis linear accelerometer, provided by STMicroelectronics. Other suitable accelerometers will be known to one of ordinary skill in the art from the description herein.

In another exemplary embodiment, sensor 102 is a sound or noise sensor, e.g., a microphone. The microphone may be configured to record any sounds made by the surgical tool during the surgery. Suitable microphones for use as sensor 102 will be known to one of ordinary skill in the art from the description herein.

Figure 2B:
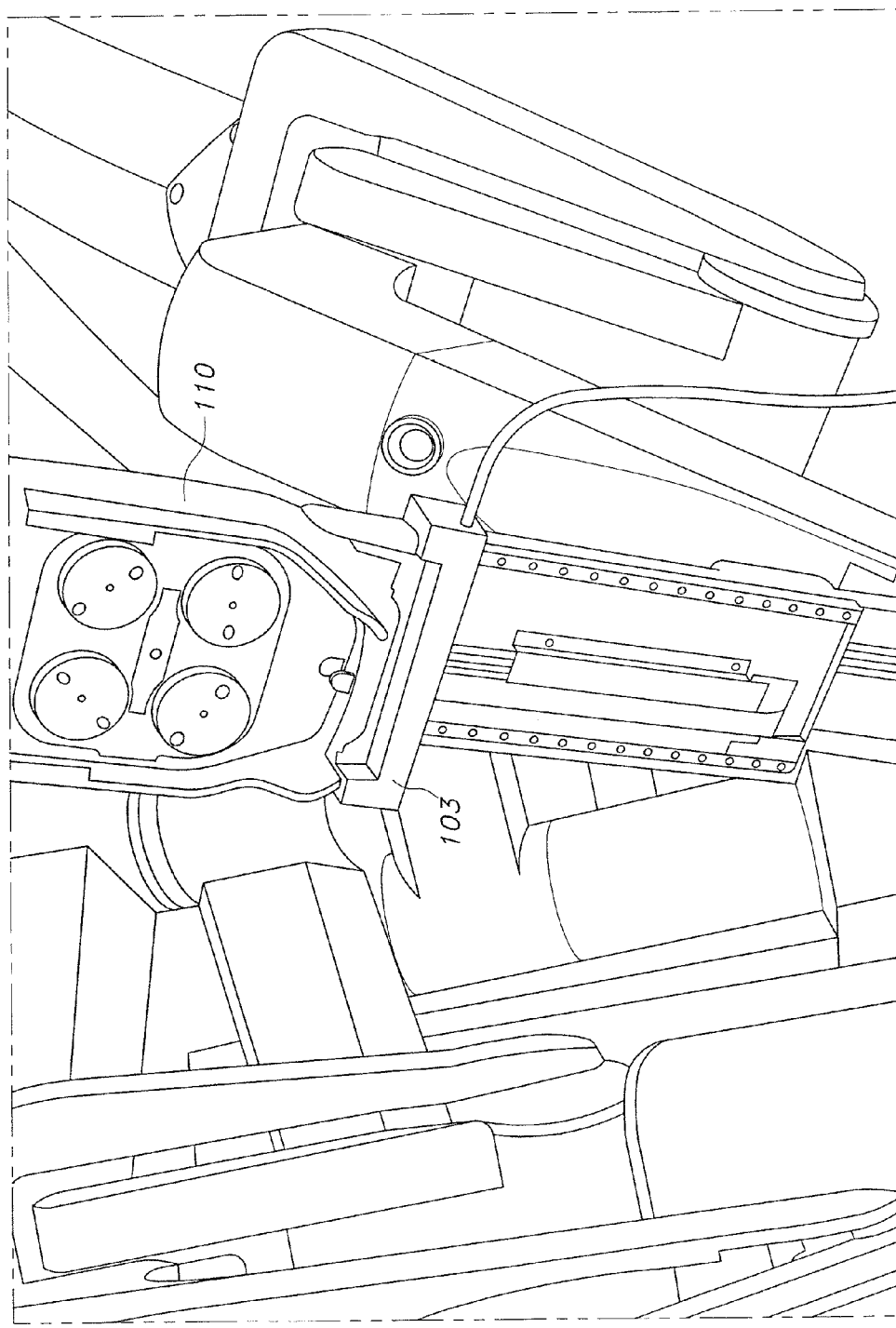
FIG. 2B depicts the sensor assembly shown in FIG. 2A mounted to a robotic surgery system.

Sensor 102 may be coupled to an armature of the robotic surgery system using a sensor assembly. FIG. 2A illustrates an exemplary sensor assembly in accordance with aspects of the present invention. In an exemplary embodiment, the sensor assembly includes sensor 102 and a sensor mount 103. FIG. 2B illustrates the exemplary sensor assembly mounted to a robotic armature of a robotic surgery system. Sensor mount 103 may affix sensor 102 to the robotic surgery system such that sensor 102 directly contacts an armature 110 of the surgery system. It may be desirable for sensor 102 to directly and/or rigidly contact the armature 110 in order to increase the transmission of vibrations from the surgical tool to sensor 102.

Figure 2C:
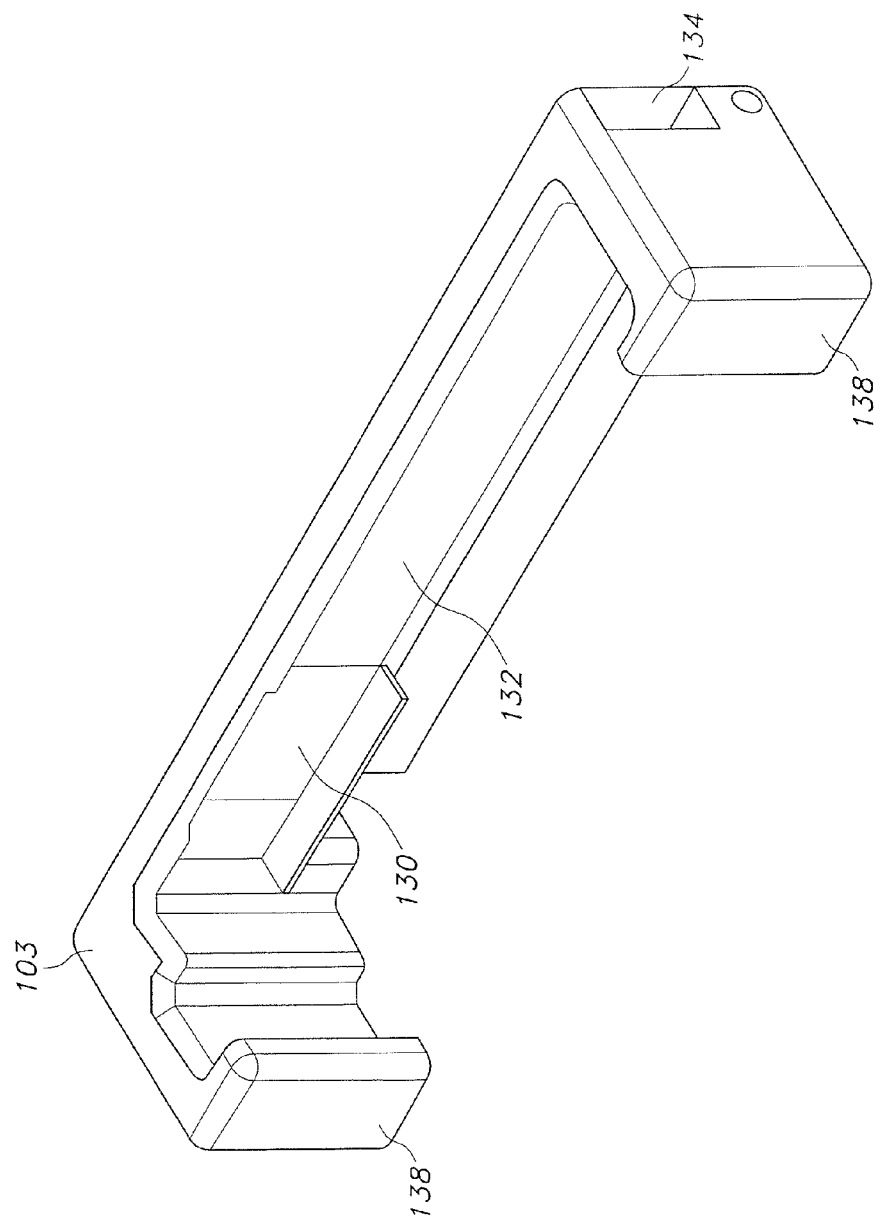
FIG. 2C depicts an exemplary embodiment of a sensor mount component of the sensor assembly shown in FIG. 2A.

FIG. 2C illustrates an exemplary sensor mount of the sensor assembly. In an exemplary embodiment, a sensor mount 103 includes a recess 130 for receiving sensor 102. Where sensor 102 uses a wire to transmit data, sensor mount 103 may optionally include a recess 132 and/or an opening 134 for the wire to pass through and attach to sensor 102. Sensor mount 103 further includes engagement surfaces 136 for engaging a robotic armature 110 of the robotic surgery system. Sensor mount 103 may further include flanges 138 for securing sensor mount 103 in place. Sensor mount 103 may couple sensor 102 to the robotic surgery system via a friction fit between engagement surfaces 136. Alternatively, sensor mount 103 may use snaps, bolts, straps, hook and loop fasteners such as VELCRO, or adhesives to couple sensor 102 to the robotic surgery system. Sensor mount 103 may desirably be adjustable such that sensor 102 can be mounted to multiple different types of robotic surgery systems or in multiple different locations of a robotic surgery system. Suitable materials for sensor mount 103 include, for example, acrylonitrile butadiene styrene (ABS) plastic. Other suitable materials for sensor mount 103 will be known to one of ordinary skill in the art from the description herein.

Sensor 102 is configured to transmit data corresponding to a sensed vibration. Desirably, sensor 102 solely transmits data corresponding to vibrations of the surgical tool or sounds made by the surgical tool. Sensor 102 may transmit the data via a wire, as shown in FIG. 1, or wirelessly, as would be understood by one of ordinary skill in the art.

As described above, sensor 102 or a supplemental sensor may sense audio signals generated by the surgical tool. Sensor 102 may be configured to detect both vibrations of the surgical tool and sounds made by the surgical tool, as both may be characterized as high frequency vibrations. Alternatively, sensor 102 may exclusively sense audio signals (as opposed to other high frequency vibrations) generated by the surgical tool. For example, sensor 102 may sense audio signals generated from the surgical tool contacting the patient during an operation. The audio signals sensed by sensor 102 may desirably be between about 15 Hz and 20,000 Hz. Sensor 102 may be configured to transmit data corresponding to the sensed audio signals.

Generally, the same vibrations that one can feel may also cause pressure waves in the air, which one could perceive as sounds. Accordingly, a separate microphone or other audio sensor may optionally be used in addition to or instead of a vibrational sensor. Because the audio and the accelerations appear similar on an oscilloscope (perhaps scaled by a factor), it is expected that no separate conversion would be needed to convert the data from a vibrational sensor from a high frequency vibration to an audio signal.

Actuators 104 are configured to be coupled to a robotic surgery system. In an exemplary embodiment, actuators 104 are configured to be coupled to a robotic surgery system in a location where actuators 104 can provide a vibration to a control handle. A robotic surgery system may include a control handle to be manipulated by an operator in operating the armature or surgical tool. Actuators 104 may be mounted directly on the control handle. Alternatively, actuators 104 may be mounted on a separate structure that is in physical contact with the control handle. It may be desirable to mount actuators 104 on a portion of the control handle removed from the area held by the operator of the control handle, in order to avoid interfering with the manipulation of the control handle by the operator.

When actuators 104 are mounted to the control handles of an existing robotic surgery system, it may be necessary to affix a counter-balance to the control handles to account for the weight of the actuators. Determination of a suitable weight and location for the counter-balance will be understood by one of ordinary skill in the art. Alternatively, a counter-balance to actuators 104 may be implemented by software in the robotic surgery system.

While two actuators 104 are illustrated, it will be understood that system 100 may include any number of actuators 104. For example, system 100 may include one actuator for each armature or surgical tool employed by the robotic surgery system. Additionally, system 100 may include an actuator 104 for each sensor 102. Finally, system 100 may include one or more actuators 104 for each control handle at the control station of the robotic surgical system. Multiple actuators may be employed on the control handles to enable system 100 to provide vibrations in multiple different directions, or provide larger vibrations. This may enhance the realism of the vibrations felt by the operator of the robotic surgery system.

Figure 10:
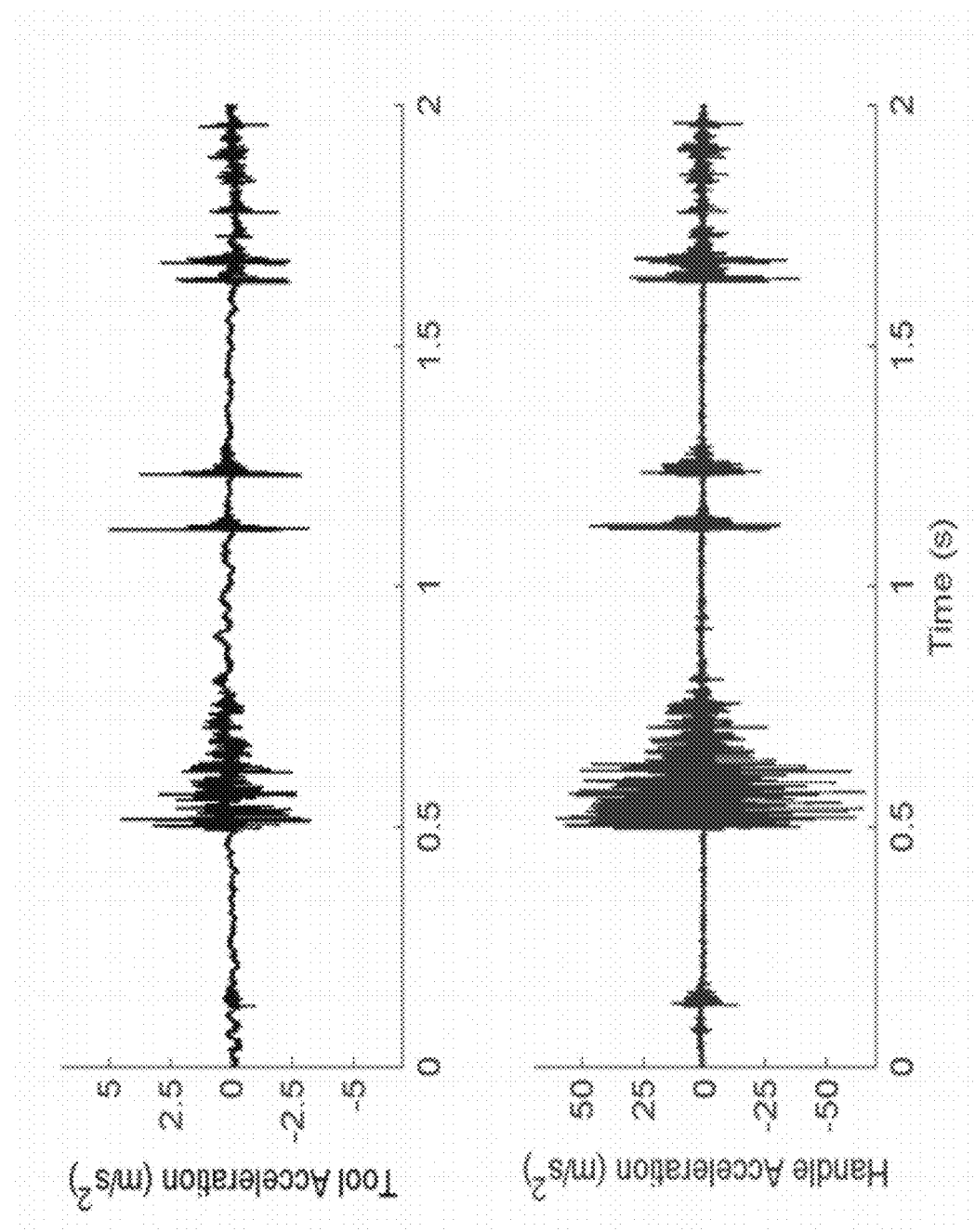
FIG. 10 is a graph depicting an exemplary vibration sensed by a sensor and an exemplary vibration provided by an actuator in accordance with aspects of the present invention.

Actuators 104 are configured to provide a vibration to the control handle. The vibrations provided by actuators 104 may desirably be high frequency vibrations, between about 10 Hz and 1000 Hz. Further, the vibrations provided by actuators 104 may match the frequency of the vibrations of the surgical tool sensed by sensor 102. FIG. 10 illustrates a graph of an exemplary vibration sensed by a sensor and a corresponding exemplary vibration provided by an actuator in accordance with an aspect of the present invention. It may be desirable to match the frequencies of the vibrations in order to accurately reproduce at the control handles the feeling of handling the surgical tool during the procedure.

Further, actuators 104 may not provide vibrations to the control handles at certain predetermined frequencies. For example, the robotic armature may have one or more resonant frequencies, or one or more natural vibrating frequencies based on operation of the motors that move the armature. Providing vibrations to the control handles at this frequency may impart a vibrating movement to the armatures, and thereby create undesirable vibrational feedback. Thus, actuators 104 may be configured not to provide vibrations at the resonant or natural vibrating frequencies of the armature in order to avoid generating unwanted feedback.

In an exemplary embodiment, actuators 104 are voice coil actuators. Suitable voice coil actuators for use as actuators 104 include, for example, voice coil linear actuators provided by H2W Technologies, Inc. or BEI Kimco Magnetics. Other suitable actuators will be known to one of ordinary skill in the art from the description herein.

Figure 3A:
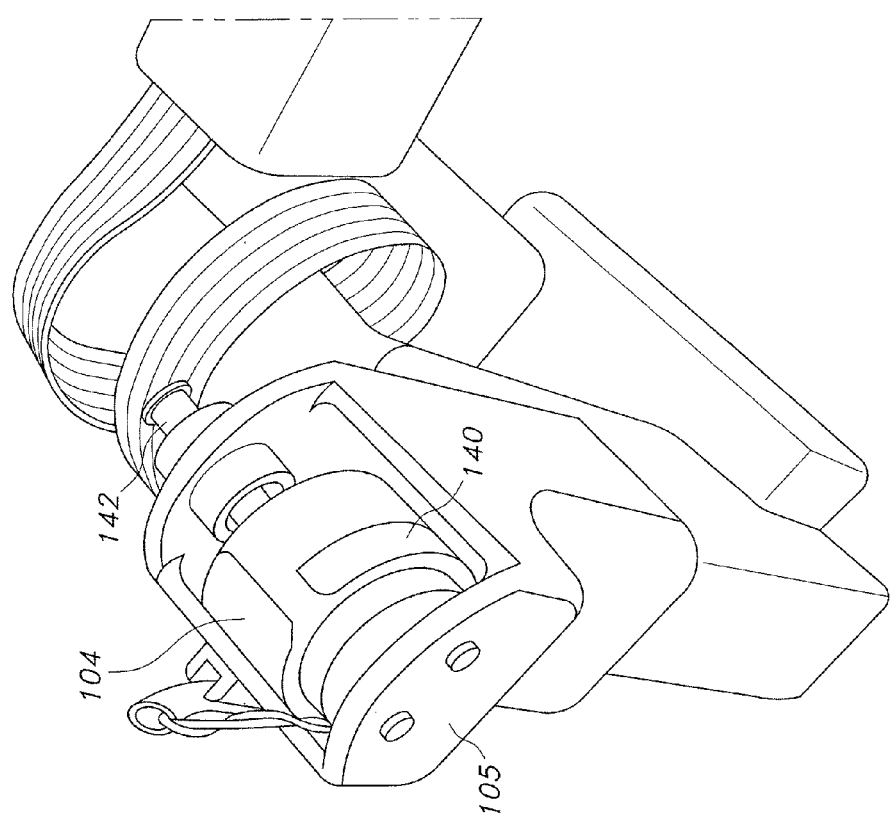
FIG. 3A depicts an exemplary embodiment of an actuator assembly of the system of FIG. 1.
Figure 3B:
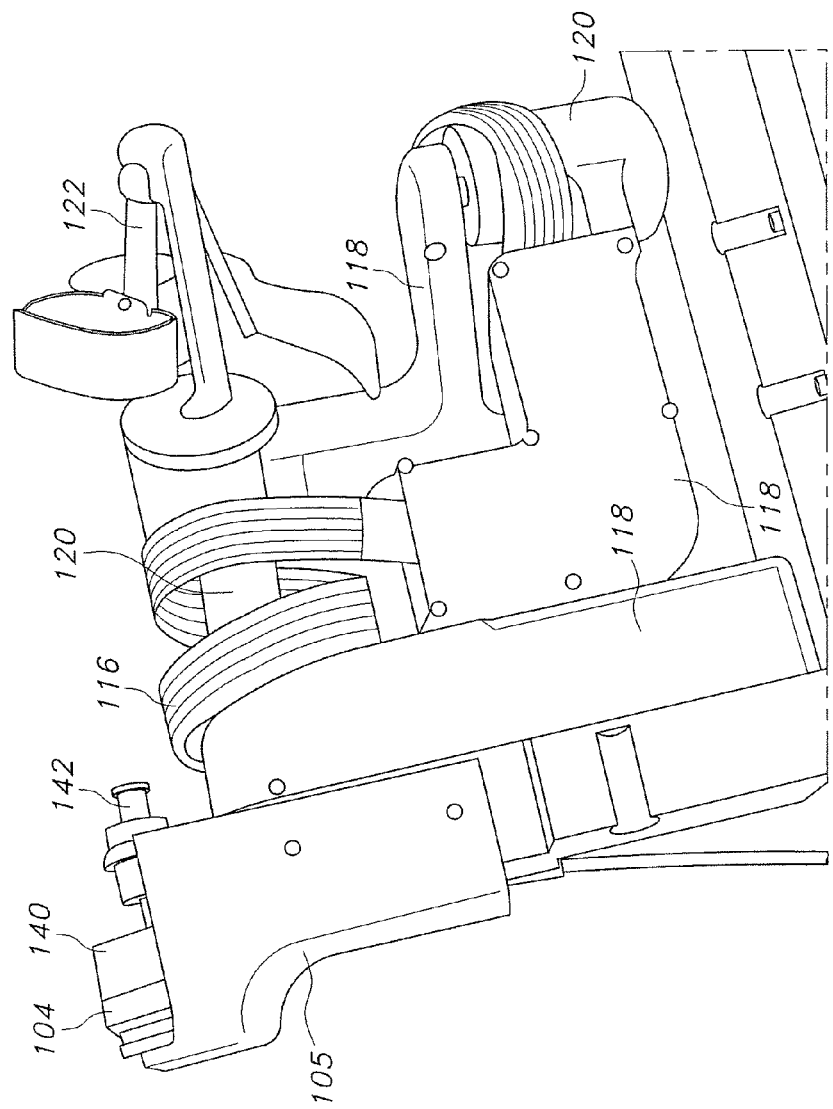
FIG. 3B depicts the actuator assembly shown in FIG. 3A mounted to a robotic surgery system.

Actuators 104 may be coupled to the control station of the robotic surgery system using an actuator assembly. FIG. 3A illustrates an exemplary actuator assembly in accordance with aspects of the present invention. In an exemplary embodiment, the actuator assembly includes actuator 104 and an actuator mount 105. FIG. 3B illustrates the exemplary actuator assembly mounted to a control handle of a robotic surgery system. In an exemplary embodiment, actuator 104 is a voice coil actuator having a wire coil 140 and a permanent magnet (not shown). Actuator mount 105 may mount the actuator 104 such that the wire coil 140 is rigidly attached to the control handle 116 and the permanent magnet is mounted on a linear bearing 142, and is centered by springs. The permanent magnet may therefore be free to move back and forth on linear bearing 142 in response to the current through the wire coil 140. Alternatively, actuator mount 105 may be configured to hold the permanent magnet stationary, and allow the wire coil to move on a linear bearing. Thus, actuator mount 105 may allow actuator 104 to provide a vibration from either the permanent magnet or the wire coil to the control handle 116.

Figure 3C:
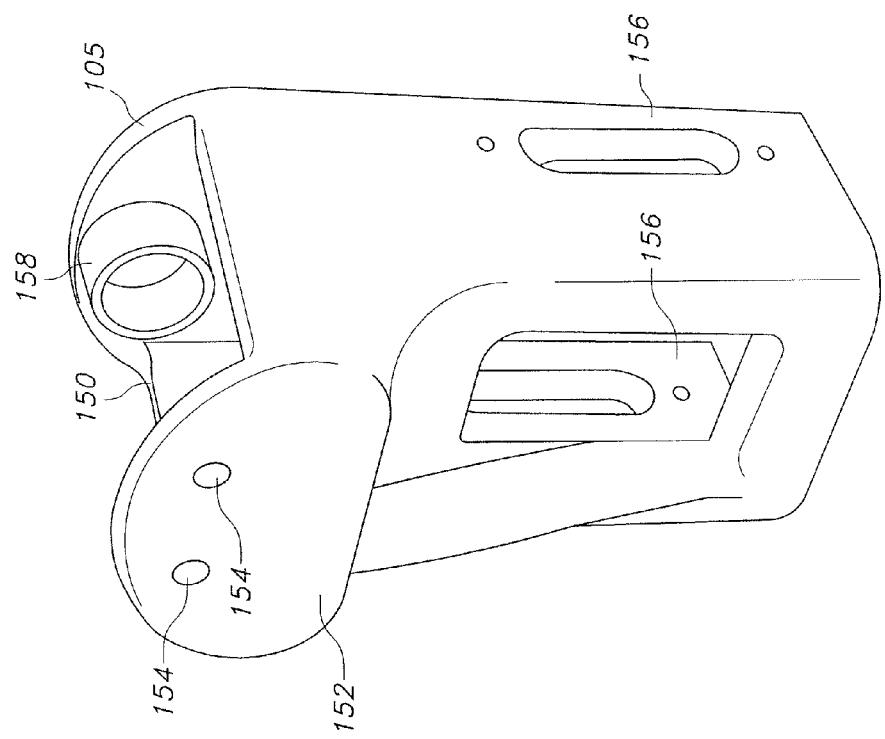
FIG. 3C depicts an exemplary embodiment of an actuator mount component of the actuator assembly shown in FIG. 3A.

FIG. 3C illustrates an exemplary actuator mount of the actuator assembly. In an exemplary embodiment, an actuator mount 105 includes a cavity 150 for receiving actuator 104. Actuator mount 105 further includes a mounting surface 152 having mounting holes 154, for rigidly securing the actuator 104 to the actuator mount 105. Actuator mount 105 further includes engagement surfaces 156 for engaging a control handle 116 of the robotic surgery system. Actuator mount 105 may further include an opening 158 for receiving a linear bearing 142 of the actuator 104. Actuator mount 105 may couple actuator 104 to the robotic surgery system via a friction fit between engagement surfaces 156. Alternatively, actuator mount 105 may use snaps, bolts, straps, hook and loop fasteners such as VELCRO, or adhesives to couple actuator 104 to the robotic surgery system. Actuator mount 105 may desirably be adjustable such that actuator 104 can be mounted to multiple different types of robotic surgery systems or in multiple different locations of a robotic surgery system. Suitable materials for actuator mount 105 include, for example, acrylonitrile butadiene styrene (ABS) plastic. Other suitable materials for actuator mount 105 will be known to one of ordinary skill in the art from the description herein.

As described above, actuators 104 may be mounted on a separate structure that is in physical contact with the control handle. As illustrated in FIG. 3B, control handle 116 may multiple fixed-length arm portions 118 and multiple joints 120, to enable control handles 116 to be movable in all three dimensions and angles of freedom. It may be desirable for actuator mount 105 to mount actuator 104 to an arm portion 118 removed from a portion of the control handle 122 grasped by an operator of the robotic surgery system, in order to avoid interfering with the manipulation of the control handle by the operator.

While actuators 104 are described above as providing vibrations to the control handle, it will be understood that actuators 104 may also provide audio signals to the operator of the control handle. Alternatively, actuators 104 may exclusively provide audio signals (as opposed to other high frequency vibrations) to an operator of the control handle. For example, actuators 104 may be speakers, and may be mounted at the control station to provide audio signals matching the audio signals generated by the surgical tool during an operation. The audio signals provided by actuators 104 may desirably be maintained between about 15 Hz and 20,000 Hz.

In one exemplary embodiment, actuators 104 are speakers. In this embodiment, the speakers are configured to be coupled to a robotic surgery system in a location where they can provide sound to a user of the robotic surgery system. For example, a robotic surgery system may include a control station, at which the speakers are mounted. It will be understood that system 100 may include any number of speakers 104. Utilizing at least two speakers may be desirable in order to provide stereo sound to the user of the robotic surgery system. Additionally, it will be understood that system 100 may include a combination of actuators 104 configured as speakers to provide audio feedback and actuators 104 configured to provide vibrations as tactile feedback.

The sounds provided by the speakers may desirably span the entire audible range. Further, the sounds provided by the speakers desirably match the sounds caused by the surgical tool sensed by sensor 102. It may be desirable to match the sounds in order to accurately reproduce at the control handles the feeling or experience of handling the surgical tool during the procedure.

In this exemplary embodiment, actuators 104 are conventional stereo computer speakers. Suitable speakers for use as actuators 104 will be known to one of ordinary skill in the art from the description herein.

Controller 106 is configured to be electrically connected with sensor 102 and actuators 104. Controller 106 is configured to receive data from sensor 102. In an exemplary embodiment, controller 106 is configured to receive data from sensor 102 corresponding to a sensed vibration of the surgical tool. Controller 106 may then process the data from sensor 102. Then, controller 106 is configured to actuate actuators 104 based on the data received from sensor 102. In an exemplary embodiment, controller 106 actuates actuators 104 such that actuators 104 provide a vibration to the control handle when sensor 102 senses a vibration of the surgical tool.

Controller 106 determines the vibrations provided by actuators 104. As described above, the vibrations provided by actuators 104 may desirably be high frequency vibrations, between about 10 Hz and 1000 Hz. Accordingly, controller 106 may only actuate actuators 104 when sensor 102 senses vibration occurring within the selected frequency range of vibrations. Further, controller 106 may not actuate actuators 104 at certain predetermined frequencies in order to avoid generating unwanted feedback, as described above.

Controller 106 may desirably amplify the vibrations provided to the control handle from actuators 104 with respect to the vibrations sensed by sensors 102. Amplifying the vibrations may provide an operator of the robotic surgery system with a superior perception of the movement of the surgical tool.

In an exemplary embodiment, controller 106 is a microcontroller. Controller 106 may have a number of data inputs and outputs corresponding to the number of sensors 102 and actuators 104, respectively. Suitable microcontrollers for use as controller 106 will be known to one of ordinary skill in the art from the description herein. Alternatively, controller 106 may comprise an analog circuit, as would be understood by one of ordinary skill in the art.

Controller 106 is configured to transmit data for actuating actuators 104. Controller 106 may transmit the data via a wire or wirelessly, as would be understood by one of ordinary skill in the art. Desirably, controller 106 solely transmits data for actuating actuators 104 when sensor 102 senses a vibration of the surgical tool. Controller 106 may further transmit data such that actuators 104 provide vibrations to the control handle in real time corresponding to sensed vibrations of the surgical tool by sensor 102. It may be desirable to actuate actuators 104 in real time to improve the precision and response time for the operator of the robotic surgery system.

While controller 106 is described above as actuating actuators 104 to provide vibrations, it will be understood that controller 106 may also actuate actuators 104 to provide an audio signal to the operator of the control handle based on the received data from sensor 102. Alternatively, controller 106 may exclusively actuate actuators 104 to provide an audio signal (as opposed to other high frequency vibrations) to the operator of the control handle.

Controller 106 may desirably perform additional signal processing steps, as set forth below, in order to provide improved vibration feedback to a user of the robotic surgery system. While the steps set forth below are described as being performed by controller 106, it will be understood that the steps may also be performed by associated processing components at sensors 102 or actuators 104.

As set forth above, sensor 102 may be an accelerometer configured to measure acceleration data in three different axes. Each axis of acceleration data may be filtered with a first-order analog low-pass filter, with a cutoff frequency of 1000 Hz for example, in order to match the bandwidth of human vibration detection. Additionally, a first order high-pass filter with a cutoff frequency of 80 Hz for example may be used to remove any DC component from each signal, and to reduce the overall response at frequencies that may generate instability.

Controller 106 may also desirably sum the three acceleration signals from sensor 102 in order to obtain one signal representative of vibrations in all directions. Because the human hand is not sensitive to vibration direction, summing multiple acceleration signals with controller 106 adequately preserves their temporal and spectral features. The summed signals may further be amplified to increase the signal-to-noise ratio during the transmission of the acceleration signals from sensors 102 to controller 106 or from controller 106 to actuators 104.

As set forth above, sensor 102 may also be an audio sensor, e.g., a microphone. Controller 106 may desirably transmit audio signals directly from sensors 102 to actuators 104 with additional processing.

System 100 may also include an amplitude controller 108. Amplitude controller 108 controls the amplitude of the vibrations provided to the control handle by actuators 104. Alternatively, where actuators 104 are speakers, amplitude controller 108 controls the volume of the sounds provided at the control station by actuators 104. Where both vibrational and auditory actuators 104 are used, it may be desirable to include separate amplitude controllers 108 for controlling the separate components. In an exemplary embodiment, amplitude controller 108 is positioned at the control station. Amplitude controller 108 may include a means for allowing an operator of the control station to adjust the amplitude of the vibrations or volume of sound provided by actuators 104. For example, amplitude controller 108 may include a knob, dial, buttons, or other data input components for setting a desired amplitude. Amplitude controller 108 may be in communication with controller 106. Amplitude controller 108 may transmit data to controller 106 based on the amplitude data input by the operator of the control station. Controller 106 may then modify the amplitude of the vibrations or volume of sound provided by actuators 104 based on the data received from amplitude controller 108. Amplitude controller 108 may control the amplitude of vibrations provided by actuators 104 such that the provided vibrations are ratiometric to the sensed vibrations. Similarly, amplitude controller 108 may control the volume of sounds provided by actuators 104 such that the provided sounds are ratiometric to the sensed sounds.

Figure 4:
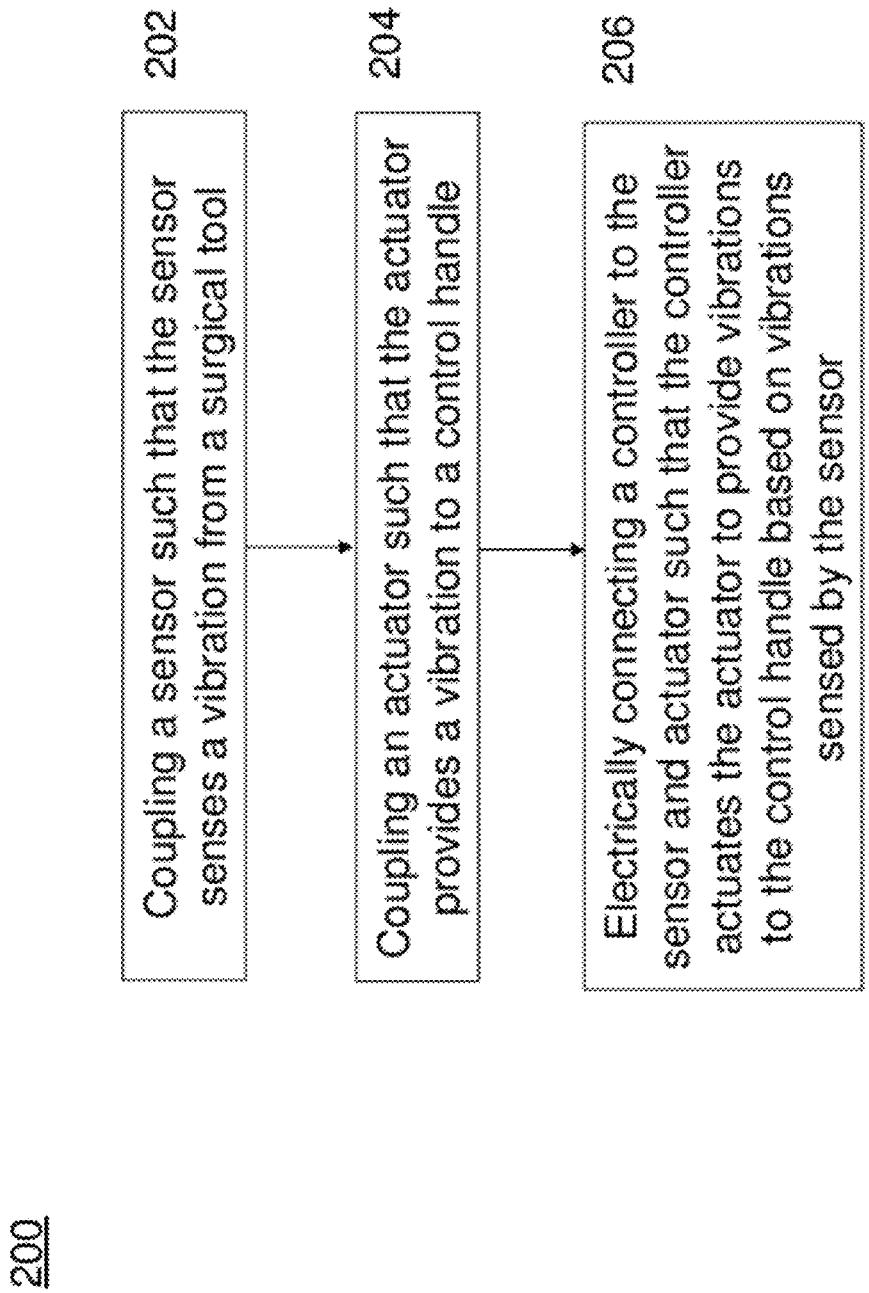
FIG. 4 is a flowchart depicting an exemplary method for configuring a robotic surgery system to provide vibration feedback during robot-assisted surgery in accordance with aspects of the present invention.

FIG. 4 is a flowchart illustrating an exemplary method 200 for configuring a robotic surgery system to provide vibration feedback during robot-assisted surgery in accordance with an aspect of the present invention. Method 200 may configure the robotic surgery system to provide tactile feedback and/or audio feedback to a user. Method 200 may be employed on robotic surgery systems including an armature for manipulating a surgical tool and a control station having a control handle for operating the armature. As an overview, method 200 includes coupling a sensor to a surgical system, coupling an actuator to a surgical system, and electrically connecting a controller with the sensor and the actuator. For the purposes of illustration, the steps of method 200 are described herein with respect to the components of system 100. Additional details of method 200 are described below.

In step 202, a sensor is coupled to the surgical system such that the sensor senses a vibration of the surgical tool. In an exemplary embodiment, sensor 102 is coupled to a robotic surgery system in a location where sensor 102 can sense a vibration of a surgical tool. As described above, sensor 102 may be mounted directly to an armature of the robotic surgery system. Sensor 102 may be mounted in an area of the robotic surgery system that is outside of a sterile area.

As described above, sensor 102 may be coupled to an armature of the robotic surgery system using a sensor mount. The sensor mount may be substantially as described above in connection with system 100.

As described above, sensor 102 is configured to transmit data corresponding to a sensed vibration. Desirably, sensor 102 solely transmits data corresponding to vibrations of the surgical tool. Sensor 102 may transmit the data via a wire or wirelessly, as would be understood by one of ordinary skill in the art.

As described above, while sensor 102 is described as sensing vibrations of the surgical tool, it will be understood that sensor 102 may also sense audio signals generated by the surgical tool. For example, sensor 102 may be a microphone coupled to the surgical system in order to sense audio signals generated from the surgical tool contacting the patient during an operation. Sensor 102 may be configured to transmit data corresponding to the sensed audio signals.

In step 204, an actuator is coupled to the surgical system such that the actuator provides a vibration to the control handle. In an exemplary embodiment, actuator 104 is coupled to a robotic surgery system in a location where actuator 104 can provide a vibration to the control handle. As described above, actuator 104 may be mounted directly on the control handle. Actuator 104 may be mounted on a separate structure that is in physical contact with the control handle.

As described above, actuator 104 may be coupled to the control station of the robotic surgery system using an actuator mount. The actuator mount may be substantially as described above with respect to system 100.

As described above, actuator 104 is configured to provide vibrations to the control handle that correspond to a sensed vibration. Desirably, the vibrations provided by actuator 104 may be high frequency vibrations, between about 10 Hz and 1000 Hz. Further, the vibrations provided by actuators 104 may match the frequency of the vibrations of the surgical tool sensed by sensor 102.

As described above, while actuators 104 are described as providing vibrations to the control handle, it will be understood that actuators 104 may also provide audio signals to the operator of the control handle. For example, actuators 104 may be speakers, and may be mounted at the control station to provide audio signals matching the audio signals generated by the surgical tool during an operation.

In step 206, a controller is electrically connected with the sensor and the actuator such that the controller receives data from the sensor and actuates the actuator. In an exemplary embodiment, controller 106 is electrically connected to sensor 102 to receive data from sensor 102 corresponding to a sensed vibration of the surgical tool. Further, controller 106 is electrically connected to actuators 104 to actuate the actuators 104 based on the data received from sensor 102. Controller 106 may actuate actuators 104 such that actuators 104 provide a vibration to the control handle when sensor 102 senses a vibration of the surgical tool. Controller 106 may only actuate actuators 104 when sensor 102 senses vibration occurring within a selected frequency range of vibrations. Controller 106 may further amplify the vibrations provided to the control handle from actuators 104 with respect to the vibrations sensed by sensors 102.

As described above, controller 106 is configured to transmit data for actuating actuators 104. Desirably, controller 106 solely transmits data for actuating actuators 104 when sensor 102 senses a vibration of the surgical tool. Controller 106 may transmit the data via a wire or wirelessly, as would be understood by one of ordinary skill in the art.

As described above, while controller 106 is described as actuating actuators 104 to provide vibrations, it will be understood that controller 106 may also actuate actuators 104 to provide an audio signal to the operator of the control handle based on the received data from sensor 102.

Method 200 may also include the step of electrically connecting an amplitude controller with the controller. In an exemplary embodiment, amplitude controller 108 is electrically connected with controller 106. Amplitude controller 108 controls the amplitude of the vibration or the volume of sound provided by the actuator 104. For example, amplitude controller 108 may control the amplitude of vibrations provided by actuators 104 such that the provided vibrations are ratiometric to the sensed vibrations.

System 100 is usable for configuring a robotic surgery system to provide tactile feedback during robot-assisted surgery. It will be understood by one of ordinary skill in the art, however, that one or more of the components of system 100 may integrated directly with a robotic surgery system. Accordingly, a robotic surgery system will now be described in accordance with aspects of the present invention.

FIG. 5A illustrates an exemplary robotic surgery system 300 in accordance with an aspect of the present invention. Robotic surgery system 300 may provide tactile feedback and/or audio feedback to a user. As an overview, system 300 includes sensors 302, actuators 304, controller 306, amplitude controller 308, robotic armatures 310, surgical tools 312, control station 314, and control handles 316. Additional details of system 300 are described below.

Figure 6:
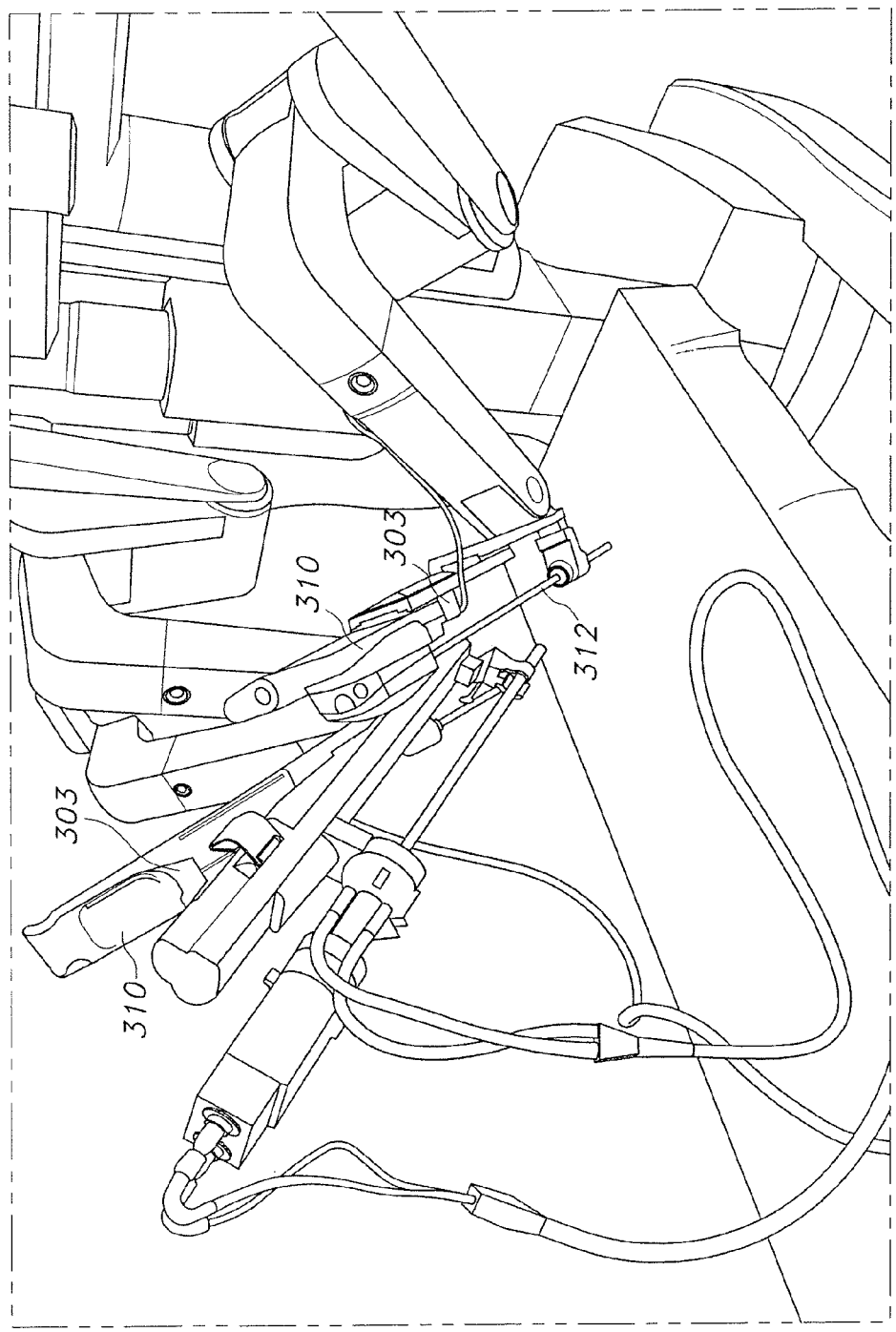
FIG. 6 depicts another exemplary embodiment of a robotic armature and surgical tool of the system of FIG. 5A.

Robotic armatures 310 are for manipulating surgical tools 312. FIGS. 5B and 6 illustrate exemplary robotic armatures and surgical tools in accordance with aspects of the present invention. In an exemplary embodiment, armatures 310 are configured to receive surgical tools 312. Surgical tools 312 may be any tools usable during a surgical procedure. Suitable surgical tools 312 will be known to one of ordinary skill in the art. Surgical tools 312 may be mounted to one or more armatures 310.

As illustrated in FIG. 6, robotic armatures 310 may include multiple fixed-length arm portion and multiple joints. Each of the joints may include actuators for bending adjacent fixed-length arm portions relative to each other. This may enable the end of each armature 310 to be movable in all three dimensions and angles of freedom. Thus, robotic armatures 310 may manipulate surgical tools 312 in all three dimensions and angles of freedom. This freedom of motion may be desirable for performing surgical procedures without limitation. Suitable robotic armatures 310 include the armatures of the DA VINCI Surgical System, provided by Intuitive Surgical, Inc. Other suitable robotic armatures 310 will be known to one of ordinary skill in the art from the description herein.

While two robotic armatures 310 are illustrated, it will be understood that system 300 may include any number of armatures 310. For example, system 300 may include an armature 310 for each surgical tool 312 employed by the robotic surgery system 300. Alternatively, system 300 may include multiple surgical tools 312 on one armature 310.

Figure 7:
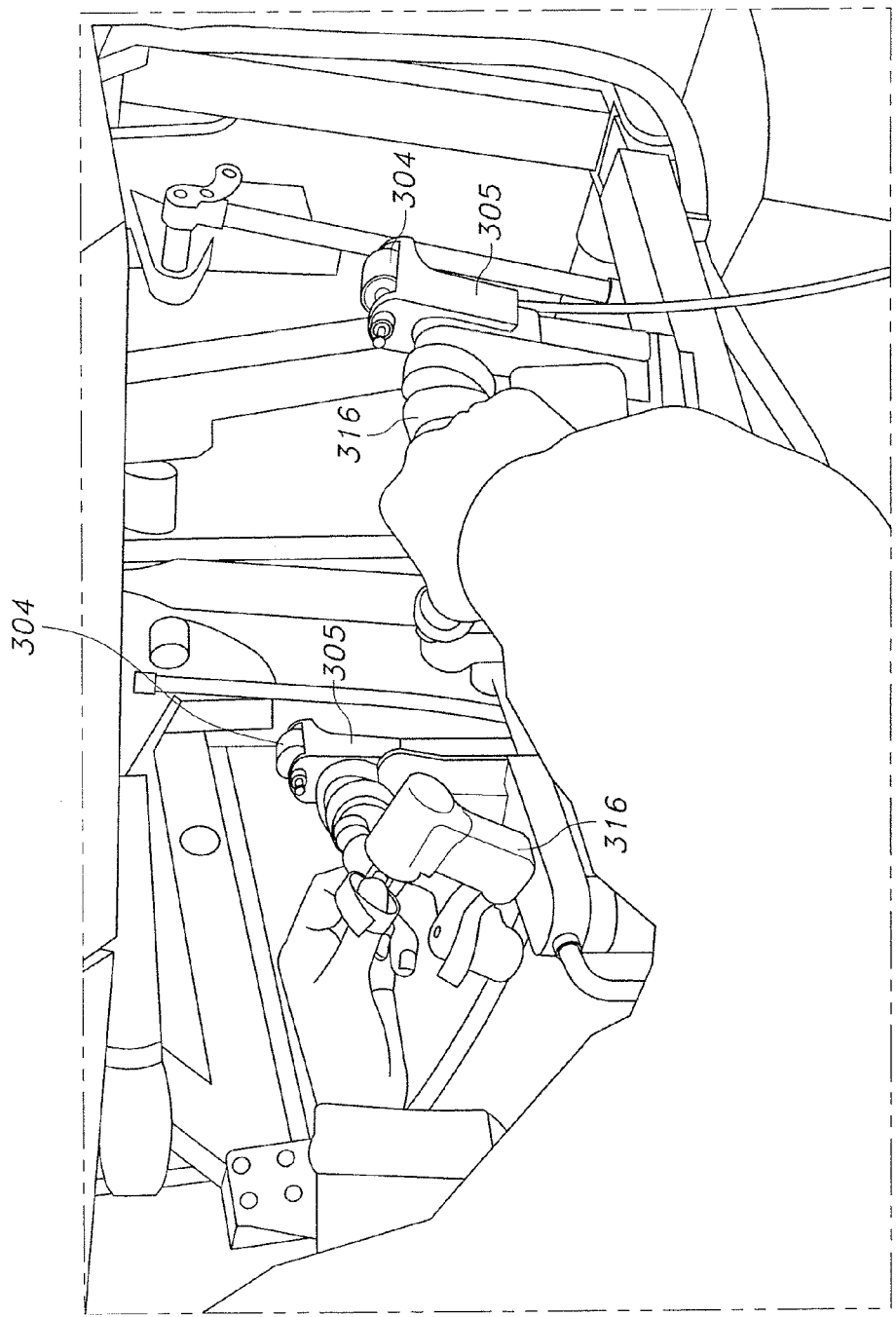
FIG. 7 depicts an exemplary control station of the system of FIG. 5A.

Control station 314 is for operating robotic armatures 310. FIG. 7 illustrates an exemplary control station in accordance with aspects of the present invention. In an exemplary embodiment, control station 314 includes control handles 316 for operating robotic armatures 310. Control station 314 allows an operator, e.g., a surgeon, to perform a robot-assisted surgery by controlling a surgical tool 312 held by robotic armatures 310. To this end, control station 314 may be electrically connected with robotic armatures 310.

Thus, control station 314 may transmit data corresponding to the motions of control handles 316 to the robotic armatures 310. Robotic armatures 310 may then move in motions corresponding to the motions of control handles 316, e.g., by actuating the actuators in the arm joints of the armatures 310. Control station may further include visual and/or audio feedback for indicating to the operator what is occurring at the location of the surgery.

FIG. 5C further illustrates exemplary control handles in accordance with aspects of the present invention. Each control handles 316 may include multiple fixed-length arm portions 318 and multiple joints 320, to enable the control handle 316 to be movable in all three dimensions and angles of freedom, similarly to armatures 310. Alternatively, control station 314 may include one or more control handles 316, each control handle operable to move a robotic armature 310 in only a single degree of freedom. Suitable control stations and control handles include the control station and control handles of the DA VINCI Surgical System, made by Intuitive Surgical, Inc. Other suitable control stations 314 and control handles 316 will be known to one of ordinary skill in the art from the description herein.

While two control handles 316 are illustrated, it will be understood that system 300 may include any number of control handles 316. For example, system 300 may include a control handle 316 for each robotic armature 310.

Sensors 302 are coupled to robotic surgery system 300. In an exemplary embodiment, sensors 302 are coupled to system 300 in a location where sensor 302 can sense a vibration of surgical tool 312. Sensors 302 may be integrated as parts of armatures 310 or surgical tool 312. It may be desirable to integrate sensors 302 into armatures 310 in order to limit the number of sensors 302 if one armature 310 may be used for multiple surgical tools 312. Additionally, it may be desirable to incorporate sensors 302 in armatures 310 so that sensors 302 may utilize the wiring and power already provided for armatures 310. Alternatively, sensors 302 may be mounted to armatures 310 near the base of surgical tools 312, as described above with respect to system 100. Sensors 302 may be mounted to armatures 310 using sensor mounts 303, which may be sensor mounts substantially as described above with respect to sensor mount 103.

As described above with respect to system 100, it will be understood that system 300 may include any number of sensors 302. In an exemplary embodiment, system 300 may include one sensor 302 for each robotic armature 310 employed by the robotic surgery system 300.

As described above with respect to system 100, sensors 302 are configured to sense a vibration of surgical tool 312. The vibrations sensed by sensors 302 may desirably be high frequency vibrations, between about 10 Hz and 1000 Hz. In an exemplary embodiment, sensors 302 are accelerometers. Suitable accelerometers for use as sensors 302 include any of the accelerometers described above with reference to sensor 102. Other suitable accelerometers will be known to one of ordinary skill in the art from the description herein.

Sensors 302 are configured to transmit data corresponding to a sensed vibration. Desirably, sensors 302 solely transmit data corresponding to vibrations of surgical tool 312. Sensors 302 may transmit the data via a wire or wirelessly, as would be understood by one of ordinary skill in the art.

As described above with respect to system 100, it will be understood that sensors 302 may also sense audio signals generated by surgical tool 312. Alternatively, sensors 302 may exclusively sense audio signals (as opposed to other high frequency vibrations) generated by surgical tool 312. For example, sensors 302 may sense audio signals generated from surgical tool 312 contacting the patient during an operation. Sensors 302 may be configured to transmit data corresponding to the sensed audio signals.

Actuators 304 are coupled to robotic surgery system 300. In an exemplary embodiment, actuators 304 are coupled to system 300 in a location where actuators 304 can provide a vibration to control handles 316, as shown in FIG. 5C. Actuators 304 may be integrated as parts of control handles 316.

Where control handles 316 have more than one fixed-length arm portion connected by one or more joints (as described above), actuators 304 may be disposed on a fixed-length arm portion removed from the portion of control handles 316 held by the operator. It may be desirable to incorporate sensors 302 in armatures 310 so that sensors 302 may utilize the wiring and power already provided for armatures 310. Alternatively, actuators 304 may be mounted to control station 314 or control hands 316, as described above with respect to system 100. Actuators 304 may be mounted to control handles 316 using actuator mounts 305, which may be actuator mounts substantially as described above with respect to actuator mount 105.

As described above with respect to system 100, it will be understood that system 300 may include any number of actuators 304. In an exemplary embodiment, system 300 may include one actuator 304 for each control handle 316 of control station 314.

Actuators 304 are configured to provide a vibration to control handle 316. The vibrations provided by actuators 304 may desirably be high frequency vibrations, between about 10 Hz and 1000 Hz. Further, the vibrations provided by actuators 304 may match the frequency of the vibrations of surgical tool 312 sensed by sensors 302.

Further, actuators 304 may not provide vibrations to control handles 316 at certain predetermined frequencies. For example, robotic armatures 310 may have one or more resonant frequencies, or one or more natural vibrating frequencies based on operation of the joints that move the armatures 310. Providing vibrations to control handles 316 at these frequencies may impart a vibrating movement to the armatures 310, and thereby create undesirable vibrational feedback. Thus, actuators 304 may be configured not to provide vibrations at the resonant or natural vibrating frequencies of the armature 310 in order to avoid generating unwanted feedback.

In an exemplary embodiment, actuators 304 are voice coil actuators. Suitable voice coil actuators for use as actuators 304 include any of the voice coil actuators described above with reference to actuators 104. Other suitable actuators will be known to one of ordinary skill in the art from the description herein.

As described above with respect to system 100, it will be understood that actuators 304 may also provide audio signals to the operator of control handles 316. Alternatively, actuators 304 may exclusively provide audio signals (as opposed to other high frequency vibrations) to an operator of control handles 316. For example, actuators 304 may be speakers, and may be mounted at control station 316 to provide audio signals matching the audio signals generated by surgical tool 312 during an operation, as shown in FIG. 5D.

Controller 306 is in communication with sensors 302 and actuators 304. Controller 306 is configured to receive data from sensors 302. In an exemplary embodiment, controller 306 is configured to receive data from sensors 302 corresponding to a sensed vibration of a surgical tool 312. Further, controller 306 is configured to actuate actuators 304 based on the data received from sensors 302. In an exemplary embodiment, controller 306 actuates actuators 304 such that actuators 304 provide a vibration to control handles 316 when sensor 302 senses a vibration of surgical tool 312.

Controller 306 determines the vibrations provided by actuators 304. As described above, the vibrations provided by actuators 304 may desirably be high frequency vibrations, between about 10 Hz and 1000 Hz. Accordingly, controller 306 may only actuate actuators 304 when sensor 302 senses vibration of surgical tool 312 occurring within the selected frequency range of vibrations. Further, controller 306 may not actuate actuators 304 at certain predetermined frequencies in order to avoid generating unwanted feedback, as described above. Controller 306 may further amplify the vibrations provided to control handles 316 from actuators 304 with respect to the vibrations sensed by sensors 302.

In an exemplary embodiment, controller 306 is a microcontroller. Controller 306 may have a number of data inputs and outputs corresponding to the number of sensors 302 and actuators 304, respectively. Controller 306 may be integrated with a master controller (not shown) for the robotic surgical system 300. In this embodiment, controller 306 may utilizing the wiring and power already in place in the robotic surgery system 300. Alternatively, controller 306 may be a separate controller, as described above with respect to system 100. Suitable microcontrollers for use as controller 306 will be known to one of ordinary skill in the art from the description herein.

Controller 306 is configured to transmit data for actuating actuators 304. Controller 306 may transmit the data via a wire or wirelessly, as would be understood by one of ordinary skill in the art. Desirably, controller 306 solely transmits data for actuating actuators 304 when sensors 302 sense a vibration of surgical tool 312. Controller 306 may further transmit data such that actuators 304 provide vibrations to control handles 316 in real time corresponding to sensed vibrations of surgical tool 312 by sensors 302. It may be desirable to actuate actuators 304 in real time to improve the precision and response time for the operator of the robotic surgery system 300.

As described above with respect to system 100, it will be understood that controller 306 may also actuate actuators 304 to provide an audio signal to the operator of control handles 316 based on the received data from sensors 302. Alternatively, controller 306 may exclusively actuate actuators 304 to provide an audio signal (as opposed to other high frequency vibrations) to the operator of control handles 316.

System 300 may also include an amplitude controller 308. FIG. 5E illustrates an exemplary amplitude controller in accordance with aspects of the present invention. Amplitude controller 308 controls the amplitude of the vibrations provided to control handles 316 by actuators 304. In an exemplary embodiment, amplitude controller 308 is positioned at control station 314. Amplitude controller 308 may be an amplitude controller substantially as described above with respect to amplitude controller 108.

Figure 8:
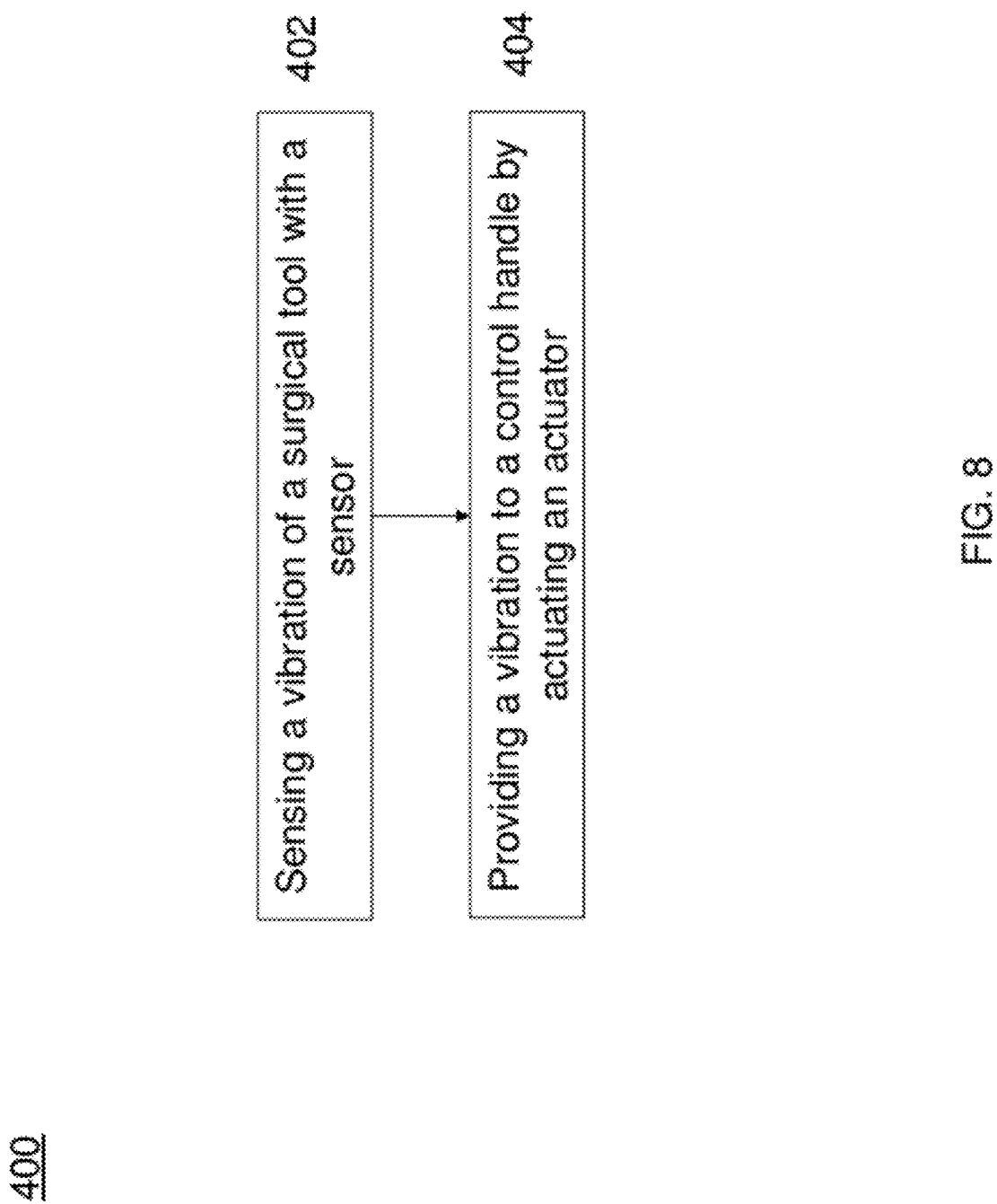
FIG. 8 is a flowchart depicting an exemplary method for providing vibration feedback during robot-assisted surgery in accordance with aspects of the present invention.

FIG. 8 is a flowchart illustrating an exemplary method 400 for providing vibration feedback during robot-assisted surgery in accordance with an aspect of the present invention. Method 400 may provide tactile feedback and/or audio feedback to a user during the robot-assisted surgery. As an overview, method 400 includes sensing a vibration of a surgical tool and actuating an actuator such that the actuator provides a vibration to a control handle. For the purposes of illustration, the steps of method 400 are described herein with respect to the components of system 300. Additional details of method 400 are described below.

Method 400 may be performed by a robotic surgery system. In an exemplary embodiment, a robotic surgery system 300 is provided. Robotic surgery system 300 includes at least one robotic armature 310 for manipulating a surgical tool 312 and a control station 314 having a control handle 316 for operating the robotic armature 310. A suitable robotic surgery system 300 is the DA VINCI Surgical System, made by Intuitive Surgical, Inc. Other suitable robotic surgery systems will be known to one of ordinary skill in the art from the description herein.

In step 402, a vibration of the surgical tool is sensed with a sensor. In an exemplary embodiment, sensor 302 senses a vibration of surgical tool 312. Sensor 302 may be coupled to robotic surgery system 300 in a location where sensor 302 can sense a vibration of surgical tool 312. As described above, sensor 302 may be integrated directly into armature 310 or surgical tool 312. Alternatively, sensor 302 may be mounted directly to armature 310 of robotic surgery system 300. Sensor 302 may be mounted in an area of robotic surgery system 300 that is outside of a sterile area.

As described above, sensor 302 is configured to transmit data corresponding to a sensed vibration. Desirably, sensor 302 solely transmits data corresponding to vibrations of surgical tool 312. Sensor 302 may transmit the data via a wire or wirelessly, as would be understood by one of ordinary skill in the art.

As described above, while sensor 302 is described as sensing vibrations of surgical tool 312, it will be understood that sensor 302 may also sense audio signals generated by the surgical tool. For example, sensor 302 may be a microphone coupled to surgical system 300 such that it senses audio signals generated from surgical tool 312 contacting the patient during an operation. Sensor 302 may be configured to transmit data corresponding to the sensed audio signals.

In step 404, a vibration is provided to the control handle by actuating an actuator. In an exemplary embodiment, controller 306 actuates actuator 304 such that actuator 304 provides a vibration to control handles 316 when sensor 302 senses a vibration of surgical tool 312. Controller 306 is in communication with sensor 302 to receive data from sensor 302 corresponding to a sensed vibration of surgical tool 312. Further, controller 306 is in communication with actuator 304 to actuate the actuators 304 based on the data received from sensor 302. Controller 306 may actuate actuators 304 such that actuators 304 provide a vibration to control handle 316 when sensor 302 senses a vibration of surgical tool 312.

Desirably, controller 306 solely transmits data for actuating actuator 304 when sensor 302 senses a vibration of the surgical tool. Controller 306 may transmit the data via a wire or wirelessly, as would be understood by one of ordinary skill in the art. Controller 306 may only actuate actuators 304 when sensor 302 senses vibration occurring within a selected frequency range of vibrations.

As described above, actuator 304 may be integrated directly into control handle 316. Alternatively, actuator 304 may be mounted on control handle 316 or on a separate structure of control station 314 that is physically connected with control handle 316.

As described above, controller 306 actuates actuator 304 to provide vibrations to control handle 316 that correspond to a sensed vibration from surgical tool 312. Desirably, the vibrations provided by actuator 304 may be high frequency vibrations, between about 10 Hz and 1000 Hz. Further, the vibrations provided by actuator 304 may match the frequency of the vibrations of surgical tool 312 sensed by sensor 302.

As described above, while actuators 304 are described as providing vibrations to the control handle, it will be understood that controller 306 may actuate actuators 304 such that they provide audio signals to the operator of control handles 316. For example, actuators 304 may be speakers, and may be mounted at the control station to provide audio signals matching the audio signals generated by surgical tool 312 during an operation.

Method 400 may also include the step of controlling the amplitude of vibration provided by the actuator to the control handle with an amplitude controller with the controller. In an exemplary embodiment, amplitude controller 308 is electrically connected with controller 306. The operator of control station 314 may control the amplitude of the vibration provided to control handles 316 by the actuator 304 using amplitude controller 308.

Figure 9:
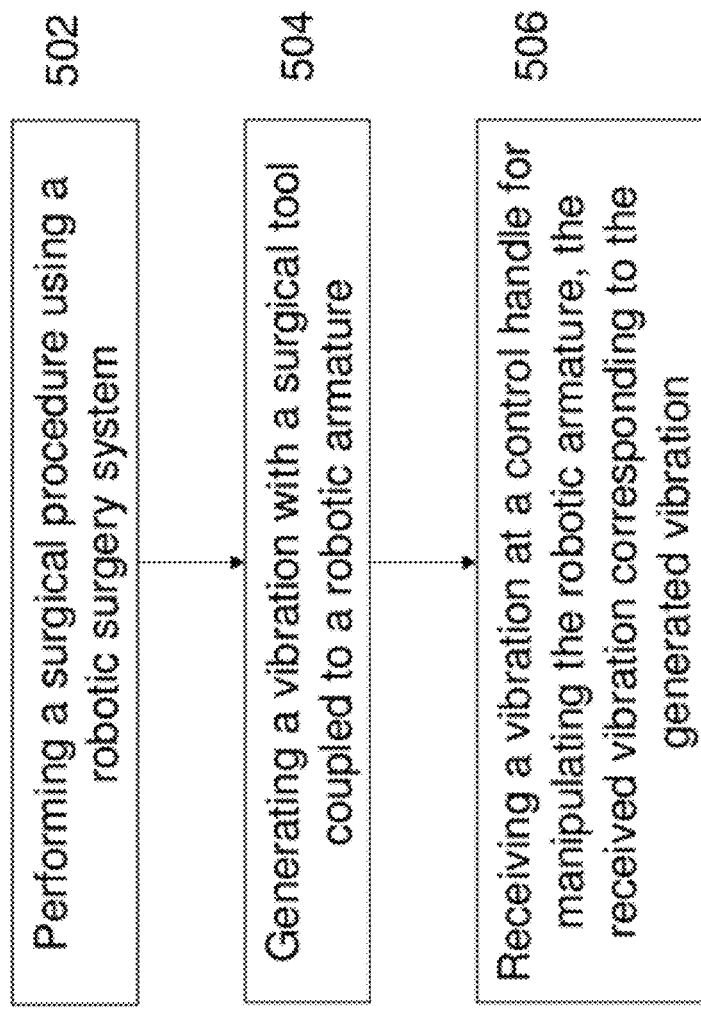
FIG. 9 is a flowchart depicting an exemplary method for performing robot-assisted surgery in accordance with aspects of the present invention.

FIG. 9 is a flowchart illustrating an exemplary method 500 for performing robot-assisted surgery in accordance with an aspect of the present invention. As an overview, method 500 includes performing a surgical procedure using a robotic surgery system, generating a vibration with a surgical tool coupled to a robotic armature, and receiving a vibration at a control handle. For the purposes of illustration, the steps of method 500 are described herein with respect to the components of system 300. Additional details of method 500 are described below.

In step 502, a surgical procedure is performed using a robotic surgery system. In an exemplary embodiment, a surgical procedure is performed using robotic surgery system 300. The surgical procedure may be any known surgical procedure including, for example, urologic, gynecologic, cardiac, oral, or plastic surgical procedures. Robotic surgery system 300 includes at least one robotic armature 310 for manipulating a surgical tool 312 and a control station 314 having a control handle 316 for operating the robotic armature 310. A suitable robotic surgery system 300 is the DA VINCI Surgical System, made by Intuitive Surgical, Inc. Other suitable robotic surgery systems will be known to one of ordinary skill in the art from the description herein.

In step 504, a vibration is generated with a surgical tool is coupled to a robotic armature. In an exemplary embodiment, surgical tool 312 is coupled to robotic armature 310. When an operator of the robotic surgery system manipulates the surgical tool 312 during the surgical procedure, surgical tool 312 generates a vibration. Sensor 302 senses a vibration of surgical tool 312.

As described above, sensor 302 is configured to transmit data corresponding to the sensed vibration. Desirably, sensor 302 solely transmits data corresponding to vibrations of surgical tool 312. Sensor 302 may transmit the data via a wire or wirelessly, as would be understood by one of ordinary skill in the art.

As described above, while surgical tool 312 is described as generating vibrations, it will be understood that surgical tool 312 may also generate audio signals. Sensor 302 may be configured to sense and transmit data corresponding to the sensed audio signals.

In step 506, a vibration is received at a control handle of the robotic surgical system. In an exemplary embodiment, controller 306 actuates actuator 304 such that actuator 304 provides a vibration to control handles 316. The operator of the robotic surgery system thereby receives a vibration through the operator's contact with the control handles 316 during the surgical procedure.

As described above, controller 306 actuates actuator 304 to provide vibrations to control handle 316 that correspond to a sensed vibration from surgical tool 312. Desirably, the vibrations provided by actuator 304 may be high frequency vibrations, between about 10 Hz and 1000 Hz. Further, the vibrations provided by actuator 304 may match the frequency of the vibrations of surgical tool 312 sensed by sensor 302.

As described above, while vibrations are received at control handles 316, it will be understood that actuators 304 may also generate audio signals. Actuators 304 may be speakers configured to generate sounds corresponding to the sensed audio signals, which may be received by an operator of the robotic surgery system 300 at the control station 314.

The above systems and methods are particularly suitable for providing tactile feedback in robotic surgery systems. While tactile feedback may include many different sensations associated with touch, the above systems and methods are directed to providing vibrations, and more particularly high-frequency vibrations, to the operator of the system.

A surgical tool may experience both forces and vibrations during a surgical procedure. It has been determined that it may be overly difficult or expensive to realistically implement force feedback to the operator of a robotic surgery system during the surgical procedure. Additionally, it has been discovered that implementing vibration feedback may be equally or more useful than force feedback to the operator during the surgical procedure. Accordingly, the above systems and methods implement vibration feedback to convey the events that take place during the surgical procedure to the operator.

It will be understood that tactile feedback can serve a critical function during manipulation of a surgical tool during surgery, e.g., for differentiating tissue types, handling suture needles, and detecting tool-tool collisions. When a robotic surgical system is employed, normal methods of tactile feedback (i.e. by direct contact between the surgeon and the surgical tool) are lost. Visual feedback employed on robotic surgery systems may be ineffective or insufficient to make up for the lack of tactile feedback. Thus, the tactile feedback provided by the above systems and methods may improve the quality of robot-assisted surgery and help surgeons to more quickly learn how to use robotic surgery systems.

Additionally, it will be appreciated that systems and methods according to this, invention can provide substantially real-time vibration feedback to users of robotic systems so that they can be provided an additional sensory feedback to guide their use of the robotic system. For example, tactile or auditory or other sensory feedback can be provided contemporaneously with the actions of the robotic system so that the experience of the user is concurrent with interactions of the robot with its environment. Such additional sensory feedback adds to the richness of the user's experience and allows optimized use of the robotic system.

Such sensory feedback is optionally selectable by a user. Depending on a particular user's preference, the additional sensory feedback can be activated, deactivated, or changed in magnitude to suit individual preferences.

Also, systems and methods according to this invention can provide vibration feedback from a wide variety of interactions between the robotic system and a subject being manipulated by the system. For example and purposes of illustration, in the context of a surgical system, the system can provide vibration feedback from the operation of one or more surgical instrument (e.g., opening or closing a grip), interaction among instruments (e.g., tool-to-tool contact), and contact between instruments and other objects in the surgical field (e.g., contacting or releasing or grabbing a suture or tissue or needle).

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A robotic surgery system comprising:
    an armature configured for manipulating a surgical tool;
    a control station, positioned remote from the armature, having a control handle configured for operating the armature;
    a sensor positioned to sense a vibration of the surgical tool, the sensor configured to sense the vibration of the surgical tool along three different axes;
    an actuator positioned to provide a vibration to the control handle of the control station; and
    a controller in communication with the sensor and the actuator, the controller being configured to receive data from the sensor corresponding to a sensed vibration, the controller being further configured to actuate the actuator based on the received data such that the actuator provides a vibration to the control handle when the sensor senses the vibration of the surgical tool,
    wherein the controller is configured to sum the vibrations sensed along the three different axes to generate a single vibration, and is configured to actuate the actuator such that the actuator provides the single vibration to the control handle along a single axis.

2. The robotic surgery system of claim 1, wherein a frequency of the vibration provided to the control handle by the actuator is maintained between about 10 Hz and about 1000 Hz.

3. The robotic surgery system of claim 1, wherein a frequency of the vibration provided to the control handle by the actuator substantially corresponds in magnitude to a frequency of the vibration of the surgical tool.

4. The robotic surgery system of claim 1, wherein the sensor is mounted to the armature.

5. The robotic surgery system of claim 1, wherein the sensor is mounted in an area outside of a sterile area of the robotic surgery system.

6. The robotic surgery system of claim 1, further comprising an amplitude controller configured to control an amplitude of the vibration provided to the control handle by the actuator.

7. The robotic surgery system of claim 1, wherein the sensor is configured to sense an audio signal generated by the surgical tool, a speaker is configured to provide an audio signal, and the controller is further configured to actuate the speaker based on the received data such that the speaker provides an audio signal to an operator of the control handle when the sensor senses the audio signal generated by the tool.

8. A method for providing vibration feedback during robot-assisted surgery, comprising the steps of:
    operating an armature of a robotic surgical system using a control handle of a remotely positioned control station of the robotic surgical system;
    sensing a vibration of a surgical tool along three different axes with a sensor while the surgical tool is coupled to the armature of the robotic surgical system; and
    actuating an actuator to provide a vibration to the control handle of the control station of the robotic surgical system when the sensor senses the vibration of the tool,
    wherein the actuating step comprises summing the vibrations along the three different axes to generate a single vibration and actuating the actuator to provide the single vibration to the control handle along a single axis.

9. The method of claim 8, the actuating step comprising providing a frequency of the vibration to the control handle between about 10 Hz and about 1000 Hz.

10. The method of claim 8, the actuating step comprising providing a frequency of the vibration to the control handle substantially corresponds to a frequency of the vibration of the surgical tool.

11. The method of claim 8, wherein the step of sensing a vibration of the surgical tool comprises sensing a vibration of the surgical tool with a sensor mounted to the armature.

12. The method of claim 8, wherein the step of sensing a vibration of the surgical tool comprises sensing a vibration of the surgical tool with a sensor mounted in an area outside of a sterile area of the robotic surgery system.

13. The method of claim 8, further comprising the step of controlling an amplitude of the vibration provided to the control handle by the actuator with an amplitude controller.

14. The method of claim 8, further comprising the steps of:
sensing a signal generated by the surgical tool with the sensor; and
actuating the actuator such that the actuator provides an audio signal to an operator of the control handle when the sensor senses the audio signal generated by the tool.

15. A robotic surgery system comprising:
an armature configured for manipulating a surgical tool;
a control station positioned remote from the armature and having a control handle configured for operating the armature;
a sensor positioned to sense a vibration generated by the surgical tool, the sensor configured to sense the vibration of the surgical tool along three different axes;
an actuator positioned to provide an audio signal to an operator of the control handle; and
a controller in communication with the sensor and the actuator, the controller being configured to receive data corresponding to a sensed signal from the sensor, the controller being further configured to actuate the actuator based on the received data such that the actuator provides an audio signal to an operator of the control handle when the sensor senses the signal generated by the tool,
wherein the controller is configured to sum the vibrations sensed for the three axes to generate a single vibration, and is configured to actuate the actuator such that the actuator provides an audio signal to the control handle based on the single vibration.

16. The robotic surgery system of claim 15, wherein a frequency of the audio signal provided to the operator of the control handle by the actuator substantially corresponds in magnitude to a frequency of a sound generated by the surgical tool.

17. The robotic surgery system of claim 15, further comprising an amplitude controller configured to control an amplitude of the audio signal provided to the operator of the control handle by the actuator.

18. A method for performing robot-assisted surgery, comprising the steps of:
manipulating a surgical tool coupled to a robotic armature of a robotic surgery system using a control handle of a control station positioned remotely from the robotic armature, thereby generating a vibration of the surgical tool, the generated vibration being generated along three different axes of the surgical tool; and
receiving a vibration at the control handle of the control station, the received vibration at the control handle corresponding to the generated vibration of the surgical tool,
wherein the received vibration constitutes a single vibration that is a sum of the vibrations generated along the three different axes of the surgical tool, and the received vibration is received along a single axis.

19. A robotic surgery system comprising:
an armature configured for manipulating a surgical tool;
a control station, positioned remote from the armature, having a control handle configured for operating the armature;
a sensor positioned to sense a vibration of the surgical tool, the sensor configured to sense the vibration of the surgical tool along three different axes;
an actuator positioned to provide a vibration at the control station; and a controller in communication with the sensor and the actuator, the controller being configured to receive data from the sensor corresponding to a sensed vibration, the controller being further configured to actuate the actuator based on the received data such that the actuator provides a vibration at the control station,
wherein the controller is configured to sum the vibrations along the three different axes to generate a single vibration, and the controller is configured to actuate the actuator such that the actuator provides the single vibration at the control station along a single axis.

20. The robotic surgery system of claim 19, wherein a frequency of the vibration provided at the control station by the actuator substantially corresponds in magnitude to a frequency of the vibration of the surgical tool.

21. The robotic surgery system of claim 19, further comprising an amplitude controller configured to control an amplitude of the vibration provided at the control station.

22. The robotic surgery system of claim 19, wherein the actuator is positioned to provide a vibration to a control handle at the control station.

23. The robotic surgery system of claim 19, wherein the actuator is a speaker configured to provide audio signals at the control station.

24. A method for providing vibration feedback during robot-assisted surgery, comprising the steps of:
operating an armature of a robotic surgical system from a remotely positioned control station of the robotic surgical system;
sensing a vibration of a surgical tool along three different axes with a sensor while the surgical tool is coupled to the armature of the robotic surgical system; and
actuating an actuator to provide a vibration at the control station of the robotic surgical system when the sensor senses the vibration of the tool,
wherein the actuating step comprises summing the vibrations along the three different axes to generate a single vibration and actuating the actuator to provide the single vibration at the control station along a single axis.

25. The method of claim 24, wherein the actuating step comprises providing a frequency of the vibration at the control station that substantially corresponds to a frequency of the vibration of the surgical tool.

26. The method of claim 24, further comprising the step of controlling an amplitude of the vibration provided at the control station by the actuator with an amplitude controller.

27. The method of claim 24, wherein the actuating step comprises providing a vibration to a control handle at the control station.

28. The method of claim 24, wherein the actuating step comprises actuating a speaker to provide audio signals at the control station.

* * * * *